US007846744B2

(12) United States Patent
Ravetch et al.

(10) Patent No.: US 7,846,744 B2
(45) Date of Patent: Dec. 7, 2010

(54) METHODS OF IDENTIFYING ANTI-INFLAMMATORY COMPOUNDS

(76) Inventors: Jeffrey V. Ravetch, 500 Park Ave., 39th Floor, New York, NY (US) 10022; Robert M Anthony, 238 E. 81st, #1A, New York, NY (US) 10028

( * ) Notice: Subject to any disclaimer, the term of this patent is extended or adjusted under 35 U.S.C. 154(b) by 0 days.

(21) Appl. No.: 12/428,402

(22) Filed: Apr. 22, 2009

(65) Prior Publication Data

US 2009/0263378 A1 Oct. 22, 2009

Related U.S. Application Data

(60) Provisional application No. 61/046,847, filed on Apr. 22, 2008, provisional application No. 61/097,344, filed on Sep. 16, 2008.

(51) Int. Cl.
*G01N 33/566* (2006.01)
*G01N 33/563* (2006.01)
*G01N 33/53* (2006.01)
*G01N 33/567* (2006.01)

(52) U.S. Cl. ........................ 436/501; 436/512; 435/7.1; 435/7.2; 435/7.21

(58) Field of Classification Search ....................... None
See application file for complete search history.

(56) References Cited

U.S. PATENT DOCUMENTS

| | | | | |
|---|---|---|---|---|
| 6,391,507 | B1 | 5/2002 | Macholdt et al. | |
| 7,064,191 | B2 | 6/2006 | Shinkawa et al. | |
| 7,427,469 | B2 * | 9/2008 | Amara et al. | 435/5 |
| 2005/0123546 | A1 | 6/2005 | Umana | |
| 2007/0048740 | A1 | 3/2007 | Isogai | |
| 2008/0025913 | A1 * | 1/2008 | Bowdish et al. | 424/1.49 |
| 2008/0206246 | A1 | 8/2008 | Ravetch | |
| 2009/0004179 | A1 | 1/2009 | Ravetch | |

FOREIGN PATENT DOCUMENTS

| | | |
|---|---|---|
| WO | WO 2007/005786 | 1/2007 |
| WO | WO 2007/055916 | 5/2007 |
| WO | WO 2007/117505 | 10/2007 |
| WO | WO 2008/057634 | 5/2008 |
| WO | WO 2009/079382 | 6/2009 |

OTHER PUBLICATIONS

Hodges et al., Activation of the lectin DC-SIGN induces an immature dendritic cell phenotype triggering Rho-GTPase activity required for HIV-1 replication, Nature Immunology, Jun. 2007, p. 569-570, vol. 8, Nature Publishing Group, USA.

Caparrós et al., DC-SIGN litigation on dendritic cells results in ERK and P13k activation and modulates cytokine production, Blood, Jan. 2006, p. 3950-3958, vol. 107, American Society of Hematology, Washington DC, USA.

Elomaa et al., Cloning of a Novel Bacteria-Binding Receptor Structurally Related to Scavenger Receptors and Expressed in a Subset of Macrophages, Cell, Feb. 1995, p. 603-609, vol. 80, Cell Press, USA.

Galustian et al.; High and Low Affinity Carbohydrate ligands revealed for murine SIGN-R1 by carbohydrate array and cell binding approaches, and differing specificities for SIGN-R3 and langerin, International Immunology, May 2004, p. 853-867, vol. 16, The Japanese Society for Immunology, Japan.

Tailleux et al.; DC-SIGN is the Major *Mycobacterium tuberculosis* Receptor on Human Dendritic Cells, Journal of Experimental Medicine, Jan. 2003, p. 121-127, vol. 197, The Rockefeller University Press, USA.

Pohlmann et al., Hepatitis C Virus Glycoproteins Interact with DC-SIGN and DC-SIGNR, Journal of Virology, Apr. 2003, p. 4070-4080, vol. 77, American Society for Microbiology, USA.

Geijtenbeck et al., Identification of DC-SIGN, a Novel Dendritic Cell-Specific ICAM-3 Receptor that Supports Primary Immune Responses, Cell, Mar. 2000, p. 575-585, vol. 100, Cell Press, USA.

Takai et al., The Study of Allergy by Japanese Researchers: a historial perspective, International Immunology, 1996, p. 1311-1316, vol. 21, No. 12, The Japanese Society for Immunology, Japan.

Lanoue et al., SIGN-R1 Contributes to Protection against Lethal Pneumococcal Infection in Mice, Journal of Experimental Medicine, Dec. 2004, p. 1383-1393, vol. 200, No. 11, The Rockefeller University Press, USA.

Kang et al., A Dominant Complement Fixation Pathway for Pneumococcal Polysaccharides Initiated by SIGN-R1 Interaction with C1q, Apr. 2006, p. 47-58, vol. 125, Cell Press, USA.

Van Der Laan et al., Regulation and Functional Involvement of Macrophage Scavenger Recepted MARCO in Clearance of Bacterica in Vivo, The Journal of Immunology, Jan. 1999, p. 939-947, vol. 162, No. 2, The American Association of Immunologists Inc., USA.

Nimmerjahn et al., The Antiinflammatory of IgG: the Intravenous IgG Paradox, Journal of Experimental Medicine, Jan. 2007, p. 11-15, vol. 204, No. 1, The Rockefeller University Press, USA.

Kaneko et al., Anti-Inflammatory Activity of Immunoglobulin G Resulting from Fc Sialylation, Science, Aug. 2006, p. 670-673, vol. 313, Science, USA.

Requena et al., Inhibition of HIV-1 Transmission in trans from dendritic cells to CD4+ T lymphocytes by natural antibodies to the CRD domain of DC-SIGN purified from breast milk and intravenous immunoglobulins, Immunology, Apr. 2008, p. 508-518, vol. 123, No. 4, Blackwell Publishing, USA.

(Continued)

*Primary Examiner*—Shulamith H. Shafer
(74) *Attorney, Agent, or Firm*—Fox Rothschild LLP; Gerard P. Norton

(57) ABSTRACT

A mammalian C-type lectin receptor type is identified which is shown to bind IgG antibodies or Fc fragments, thus inducing IVIG-related reversal of inflammation associated with various immune disorders. The identification of a DC-SIGN receptor type which interacts with IgG to promote a biological response reducing inflammation associated with immune disorders provides for methods of screening and selecting compounds which may be useful in treating various immune disorders by acting to modulate a DC-SIGN$^{(+)}$ cell to signal a second effector macrophage, causing an increase in expression of the FcγRIIB receptor and in turn inhibiting a cellular-mediated inflammatory response.

15 Claims, 11 Drawing Sheets

OTHER PUBLICATIONS

Anthony et al., "Recapitulation of IVIG anti-inflammatory activity with a recombinant IgG Fc", Science, Apr. 2008, p. 373-376, vol. 320, No. 5874, American Association for the Advancement of Science, High Wire Press, USA.

Weikert et al., "Engineering Chinese Hamster Ovary cells to Max Sialic Acid Content of Recombinant Glycoprotein", Nature Biotechnology, Nov. 1999, p. 1116-1121, vol. 17, Nature America, Inc., USA.

Boruchov, A.M. et al., "Activating and Inhibitory IgG Fc Receptors on Human DCs Mediate Opposing Functions", The Journal of Clinical Investigation, Oct. 2005, p. 2914-2923, vol. 115, No. 10., JCI, USA.

International Search Report, International Application No. PCT/US07/08396 (WO2007/117505), Aug. 2008, World Intellectual Property Organization, Geneva.

International Search Report, International Application No. PCT/US06/41791 (WO2007/055916), Aug. 2007, World Intellectual Property Organization, Geneva.

International Search Report, International Application No. PCT/US07/72771 (WO2008057634), Aug. 2008, World Intellectual Organization, Geneva.

International Search Report, International Application No. PCT/US08/86622 (WO2009079382), Mar. 2009, World Intellectual Organization, Geneva.

* cited by examiner

SEQUENCE LISTING

```
<160> NUMBER OF SEQ ID NOS: 4

<210> SEQ ID NO 1
<211> LENGTH: 4266
<212> TYPE: DNA
<213> ORGANISM: Homo sapiens

<400> SEQUENCE: 1

tggggtgaca tgagtgactc caaggaacca agactgcagc agctgggcct cctggaggag      60

gaacagctga gaggccttgg attccgacag actcgaggat acaagagctt agcagggtgt     120

cttggccatg gtcccctggt gctgcaactc ctctccttca cgctcttggc tgggctcctt     180

gtccaagtgt ccaaggtccc cagctccata agtcaggaac aatccaggca agacgcgatc     240

taccagaacc tgacccagct taaagctgca gtgggtgagc tctcagagaa atccaagctg     300

caggagatct accaggagct gacccagctg aaggctgcag tgggtgagct tccagagaaa     360
```

-continued

```
tctaagctgc aggagatcta ccaggagctg acccggctga aggctgcagt gggtgagctt    420
ccagagaaat ctaagctgca ggagatctac caggagctga cctggctgaa ggctgcagtg    480
ggtgagcttc cagagaaatc taagatgcag gagatctacc aggagctgac tcggctgaag    540
gctgcagtgg gtgagcttcc agagaaatct aagcagcagg agatctacca ggagctgacc    600
cggctgaagg ctgcagtggg tgagcttcca gagaaatcta agcagcagga gatctaccag    660
gagctgaccc ggctgaaggc tgcagtgggt gagcttccag agaaatctaa gcagcaggag    720
atctaccagg agctgaccca gctgaaggct gcagtggaac gcctgtgcca cccctgtccc    780
tgggaatgga cattcttcca aggaaactgt tacttcatgt ctaactccca gcggaactgg    840
cacgactcca tcaccgcctg caaagaagtg gggggcccagc tcgtcgtaat caaaagtgct    900
gaggagcaga acttcctaca gctgcagtct tccagaagta accgcttcac ctggatggga    960
ctttcagatc taaatcagga aggcacgtgg caatgggtgg acggctcacc tctgttgccc   1020
agcttcaagc agtattggaa cagaggagag cccaacaacg ttggggagga agactgcgcg   1080
gaatttagtg gcaatggctg gaacgacgac aaatgtaatc ttgccaaatt ctggatctgc   1140
aaaaagtccg cagcctcctg ctccagggat gaagaacagt ttctttctcc agcccctgcc   1200
accccaaacc cccctcctgc gtagcagaac ttcacccccct tttaagctac agttccttct   1260
ctccatcctt cgaccttcac aaaatctctg ggactgttct ttgtcagatt cttcctcctt   1320
tagaaggctg ggtcccattc tgtccttctt gtcatgcctc caatttcccc tggtgtagag   1380
cttgttttc tggcccatcc ttggagcttt atgagtgagc tggtgtggga tgcctttggg    1440
ggtggacttg tgttccaaga atccactctc tcttcctttt ggagattagg atatttgggt   1500
tgccatgtgt agctgctatg tcccctgggg cgttatctca tacatgcaaa cctaccatct   1560
gttcaacttc cacctaccac ctcctgcacc cctttgatcg gggacttact ggttgcaaga   1620
gctcattttg caggctggaa gcaccaggga attaattccc ccagtctacc aatggcaccc   1680
agagagggca tggaggctcc acgcaacccc ttccaccccc acatcttcct ttgtcttata   1740
catggcttcc atttggctgt ttctaagttg tattctttat tttattatta ttattactat   1800
ttttcgagat ggagtttcac tcttgtcgct caggctggag tgccatggcg cgatcttggc   1860
tcactgcaac ctctgcctcc cgggttcaag tgattctcct gcctcagcct cacgagtagc   1920
tggaattaca ggcaggcgcc accaggcccg gctaattttt tgtattttta gtacagacgg   1980
ggtttctccg tgttggtcag gctggtcttg aactcccgac ctcagatgat ctgcccgcct   2040
cggcctccca aaattgctgg gattacaggt gtgagccacc gcgcctggcc tattattttt   2100
tgtaagaata aaacaggttt actgggattt gggactctga acagttctgt ctctactacc   2160
tgatctcctc ctaccacgac tttgggatct agaggagctt tggctccggc tgtgacggct   2220
ccggccgttc tcactgcggc tgcaccggcc cccgctgcgg tcactatttc ttcctctgct   2280
tggtgaattg tgcctctcct ggctctttga catgtgctag tgagatttct tccttttcct   2340
ttcggattcc ccatttcttt tgtaggaatg gtctggacta gggttctcct tccccgcagc   2400
ctgtagtatt catcgtggtg gcccatcctc tctctcccct tggagctctt gccaaaggag   2460
gagacaagca gaggtctcta ttggatttct caacacctga agaaagttgc agtgttttcc   2520
tcttggacat tgttgtattt caaataaacc acaaatcatc attttccacc gagccactgg   2580
gcagaattca cactgaagct gtcgtcctgc gtacatacca tcgtccgtta aacagagaaa   2640
gagctgcttg gcattcttct tccgactggt actgaacata tatacttgcc cctcaggtga   2700
```

-continued

```
ggttccaagt tgcaactgac cttgaactga atcactctcc ccacgttatt ttttaattac   2760

tattttttttt taaagatggg gtcttgctct gtcgccaggc tggagtgcag tggcgcgatc   2820

taggctcact gcaacttccg cctcccgggt tcaagcgatt ctcctgcctc agcctcccga   2880

gtagctggga ctctactaaa agtacaaaaa ttagctggcg tgcaccaccg cgcccagcta   2940

attcttgtat ttttggtaga gacggggttt caacatgttg accaggatgg tctcgatctc   3000

ttgacctcgt gattcgcccg ccgcgtcctc ccaaagtgct gggattacag gcctgagcca   3060

ccgcgcccag tctctcccca cgttcttgaa ctcgggcagc acatcctcac agaaatctag   3120

gaactgttgg taggtttctt cctcgctgta ctccaggctt gcttcggagt catagtcatc   3180

cctcctgcac tgctcctttc caaacactgt aaacatgctt ttaataagaa gggtaggact   3240

ggatgttggg aaatcatgtg aacatctatc tccaaatctg caagctcctg ttttactgta   3300

gaagggacaa ttaactccat ccttctccat gactctgaaa tccaaggggg ggttccgggt   3360

tttgccatgt ggcgccattt tccaactcat tttcagcctg atccagcatc ttctggacag   3420

cttccggttt ttgtttcttc tgtcgtttct gttcctcctc ctctctctct ttcctctgct   3480

gttcttccca ttgttccttt aactttcgct cttgttcttg ccgttttcta gccacctctt   3540

ccttttcctt ctttattctg aattcttctt gtgccttctg ctctctcagc aaccactcct   3600

catgtaatct ttgcctctct cttccccata gcttttctag ttgttgtttt tcaataaaag   3660

tgtcctcctc tttctgtgag agtcctgagt ccctcagtgg agcaagttcc tgctggcgtt   3720

tctttcgttt ctccttcttc agggcggccc tgtacttttt gtggcttggt ttctctggaa   3780

atgtcacctt ttcgggcgca gccatcttgc cggcaccgcc ccgcccctct agttgtatcc   3840

tttataataa aatggtaaac attgtaaccg cagattcagc ccaatctggt tcaactttgt   3900

gtaataaaat ggcgagttgt ttttcagttg tcgtggaccc ccaggttgca agttacatac   3960

cctgggcatg tccagatgaa cgaagcgtgc aaatccacgt ggaacctaag tgctcagact   4020

gaggaacagg gactgagtta agaagtggac accacgtggc atgatccttg atccaatcag   4080

attgagccct ggcgtgatcc agtcagatca agcctcctga atcccctcat tacaagatcc   4140

aatcatatca tgcctcacta ccctctgtat ataaaatctg ccccagcctc caacttggag   4200

agacagattt gggccagact cctgtgtcct tgcttggctg ccttgcaata aatttttctc   4260

tctaca                                                               4266


<210> SEQ ID NO 2
<211> LENGTH: 404
<212> TYPE: PRT
<213> ORGANISM: Homo sapiens

<400> SEQUENCE: 2

Met Ser Asp Ser Lys Glu Pro Arg Leu Gln Gln Leu Gly Leu Leu Glu
1               5                   10                  15

Glu Glu Gln Leu Arg Gly Leu Gly Phe Arg Gln Thr Arg Gly Tyr Lys
            20                  25                  30

Ser Leu Ala Gly Cys Leu Gly His Gly Pro Leu Val Leu Gln Leu Leu
        35                  40                  45

Ser Phe Thr Leu Leu Ala Gly Leu Leu Val Gln Val Ser Lys Val Pro
    50                  55                  60

Ser Ser Ile Ser Gln Glu Gln Ser Arg Gln Asp Ala Ile Tyr Gln Asn
65                  70                  75                  80

Leu Thr Gln Leu Lys Ala Ala Val Gly Glu Leu Ser Glu Lys Ser Lys
                85                  90                  95
```

-continued

```
Leu Gln Glu Ile Tyr Gln Glu Leu Thr Gln Leu Lys Ala Ala Val Gly
            100                 105                 110

Glu Leu Pro Glu Lys Ser Lys Leu Gln Glu Ile Tyr Gln Glu Leu Thr
        115                 120                 125

Arg Leu Lys Ala Ala Val Gly Glu Leu Pro Glu Lys Ser Lys Leu Gln
    130                 135                 140

Glu Ile Tyr Gln Glu Leu Thr Trp Leu Lys Ala Ala Val Gly Glu Leu
145                 150                 155                 160

Pro Glu Lys Ser Lys Met Gln Glu Ile Tyr Gln Glu Leu Thr Arg Leu
                165                 170                 175

Lys Ala Ala Val Gly Glu Leu Pro Glu Lys Ser Lys Gln Gln Glu Ile
            180                 185                 190

Tyr Gln Glu Leu Thr Arg Leu Lys Ala Ala Val Gly Glu Leu Pro Glu
        195                 200                 205

Lys Ser Lys Gln Gln Glu Ile Tyr Gln Glu Leu Thr Arg Leu Lys Ala
    210                 215                 220

Ala Val Gly Glu Leu Pro Glu Lys Ser Lys Gln Gln Glu Ile Tyr Gln
225                 230                 235                 240

Glu Leu Thr Gln Leu Lys Ala Ala Val Glu Arg Leu Cys His Pro Cys
                245                 250                 255

Pro Trp Glu Trp Thr Phe Phe Gln Gly Asn Cys Tyr Phe Met Ser Asn
            260                 265                 270

Ser Gln Arg Asn Trp His Asp Ser Ile Thr Ala Cys Lys Glu Val Gly
        275                 280                 285

Ala Gln Leu Val Val Ile Lys Ser Ala Glu Glu Gln Asn Phe Leu Gln
    290                 295                 300

Leu Gln Ser Ser Arg Ser Asn Arg Phe Thr Trp Met Gly Leu Ser Asp
305                 310                 315                 320

Leu Asn Gln Glu Gly Thr Trp Gln Trp Val Asp Gly Ser Pro Leu Leu
                325                 330                 335

Pro Ser Phe Lys Gln Tyr Trp Asn Arg Gly Glu Pro Asn Asn Val Gly
            340                 345                 350

Glu Glu Asp Cys Ala Glu Phe Ser Gly Asn Gly Trp Asn Asp Asp Lys
        355                 360                 365

Cys Asn Leu Ala Lys Phe Trp Ile Cys Lys Lys Ser Ala Ala Ser Cys
    370                 375                 380

Ser Arg Asp Glu Glu Gln Phe Leu Ser Pro Ala Pro Ala Thr Pro Asn
385                 390                 395                 400

Pro Pro Pro Ala


<210> SEQ ID NO 3
<211> LENGTH: 1220
<212> TYPE: DNA
<213> ORGANISM: Mus musculus

<400> SEQUENCE: 3

cccatgcacc aggggacagc ggcaaccatg agtgactcca cagaagccaa gatgcagcct      60

cttagctcca tggacgatga tgagttgatg gtcagcggca gcaggtattc tattaaaagc     120

tccagactac gaccaaattc tggaatcaag tgtttggcag gatgctcggg acacagccaa     180

gtccccttgg tcctgcagct gctctccttc ctgttcttgg ctgggctcct gctgatcatt     240

cttttccaag tctccaaaac cccaaatacc gagaggcaga aggaacaaga gaagatcctc     300

caggaactga cccagctgac agatgagctt acgtccagga tccccatctc ccaagggaag     360
```

-continued

```
aatgagtcca tgcaggcgaa gatcactgag caactgatgc agctgaaaac tgaactcttg    420

tccaggattc ccatcttcca ggggcagaat gagtccatac aagagaagat ctctgagcaa    480

ctgatgcagc tgaaggctga acttctttcc aagatctcca gcttcccggt aaaggatgat    540

tctaagcagg agaagatcta ccaacagctg gtacagatga agactgaact cttccgcctg    600

tgtcgactct gcccctggga ctggacattc ctcctaggaa attgttactt cttctccaag    660

tcccagcgga actggaatga cgccgtcaca gcttgcaaag aagtgaaggc tcaactagtc    720

atcatcaata gtgatgaaga gcagaccttc ctgcagcaga cttctaaggc taaaggacca    780

acctggatgg gcctgtcaga cctgaagaag gaggccacgt ggctctgggt agatggttct    840

actctgtcat ccagattcca gaaatattgg aatagagggg agcctaacaa catcggtgag    900

gaagactgtg tcgaatttgc tggggatggc tggaatgact ctaaatgtga actcaaaaag    960

ttctggatct gcaagaagtc tgcaacccca tgcactgaag gctagctcat ctccgctcct   1020

accttcatgc cattctgcca ggcacatgga tgtgcctcac tttcgtgcca gctccttctt   1080

cctgcctgtt ggcctcagga tcgtgaaaaa ggctctggga ttcttctttt tatcagattt   1140

ttcatcctct gcatttatca tagtttcatt tctgttgatg tgataaaact ctctaaaaaa   1200

aaaaaaaaaa aaaaaaaaaa                                                1220
```

<210> SEQ ID NO 4
<211> LENGTH: 325
<212> TYPE: PRT
<213> ORGANISM: Mus musculus

<400> SEQUENCE: 4

```
Met Ser Asp Ser Thr Glu Ala Lys Met Gln Pro Leu Ser Ser Met Asp
1               5                   10                  15

Asp Asp Glu Leu Met Val Ser Gly Ser Arg Tyr Ser Ile Lys Ser Ser
            20                  25                  30

Arg Leu Arg Pro Asn Ser Gly Ile Lys Cys Leu Ala Gly Cys Ser Gly
        35                  40                  45

His Ser Gln Val Pro Leu Val Leu Gln Leu Leu Ser Phe Leu Phe Leu
    50                  55                  60

Ala Gly Leu Leu Leu Ile Ile Leu Phe Gln Val Ser Lys Thr Pro Asn
65                  70                  75                  80

Thr Glu Arg Gln Lys Glu Gln Glu Lys Ile Leu Gln Glu Leu Thr Gln
                85                  90                  95

Leu Thr Asp Glu Leu Thr Ser Arg Ile Pro Ile Ser Gln Gly Lys Asn
            100                 105                 110

Glu Ser Met Gln Ala Lys Ile Thr Glu Gln Leu Met Gln Leu Lys Thr
        115                 120                 125

Glu Leu Leu Ser Arg Ile Pro Ile Phe Gln Gly Gln Asn Glu Ser Ile
    130                 135                 140

Gln Glu Lys Ile Ser Glu Gln Leu Met Gln Leu Lys Ala Glu Leu Leu
145                 150                 155                 160

Ser Lys Ile Ser Ser Phe Pro Val Lys Asp Asp Ser Lys Gln Glu Lys
                165                 170                 175

Ile Tyr Gln Gln Leu Val Gln Met Lys Thr Glu Leu Phe Arg Leu Cys
            180                 185                 190

Arg Leu Cys Pro Trp Asp Trp Thr Phe Leu Leu Gly Asn Cys Tyr Phe
        195                 200                 205

Phe Ser Lys Ser Gln Arg Asn Trp Asn Asp Ala Val Thr Ala Cys Lys
```

-continued

```
    210                 215                 220

Glu Val Lys Ala Gln Leu Val Ile Ile Asn Ser Asp Glu Glu Gln Thr
225                 230                 235                 240

Phe Leu Gln Gln Thr Ser Lys Ala Lys Gly Pro Thr Trp Met Gly Leu
                245                 250                 255

Ser Asp Leu Lys Lys Glu Ala Thr Trp Leu Trp Val Asp Gly Ser Thr
            260                 265                 270

Leu Ser Ser Arg Phe Gln Lys Tyr Trp Asn Arg Gly Glu Pro Asn Asn
        275                 280                 285

Ile Gly Glu Glu Asp Cys Val Glu Phe Ala Gly Asp Gly Trp Asn Asp
    290                 295                 300

Ser Lys Cys Glu Leu Lys Lys Phe Trp Ile Cys Lys Lys Ser Ala Thr
305                 310                 315                 320

Pro Cys Thr Glu Gly
                325
```

METHODS OF IDENTIFYING ANTI-INFLAMMATORY COMPOUNDS

CROSS-REFERENCE TO RELATED APPLICATION

This application claims priority to U.S. provisional patent application Ser. No. 61/046,847, filed Apr. 22, 2008, and U.S. provisional patent application Ser. No. 61/097,344, filed Sep. 16, 2008, herein incorporated by reference in their entirety.

STATEMENT REGARDING FEDERALLY SPONSORED RESEARCH

The invention described herein was supported in whole or in part by grants from the National Institutes of Health (Grant No. AI034662). The U.S. Government has certain rights in this invention.

FIELD OF THE INVENTION

The present invention relates to methods of identifying compounds useful in treating an autoimmune disease. More specifically, the present invention relates to various methods of screening and selecting for compounds, such as IgG antibodies or biologically relevant fragments thereof, which are useful in treating patients suffering from an immune system disorder.

BACKGROUND OF THE INVENTION

The interaction of antibodies and antibody-antigen complexes with cells of the immune system effects a variety of responses, including antibody dependent cell-mediated cytotoxicity (ADCC) and complement dependent cytotoxicity (CDC), phagocytosis, inflammatory mediator release, clearance of antigen, and antibody half-life. Antibody constant domains are not involved directly in binding an antibody to an antigen, but exhibit various effector functions. Depending on the amino acid sequence of the constant region of their heavy chains, antibodies or immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, and IgG4; IgA1 and IgA2. Papain digestion of antibodies produces two identical antigen binding fragments, called Fab fragments, each with a single antigen binding site, and a residual "Fc" fragment, whose name reflects its ability to crystallize readily. The Fc region is central to the effector functions of antibodies.

It is known that administration of intravenous IgG (IVIG) mediates both pro- and anti-inflammatory activities through interactions mediated by its Fc fragment. Thus, IVIG is known as a therapeutic preparation which has been approved for the treatment of patients suffering from a number of autoimmune diseases, including immune-mediated thrombocytopenia, chronic inflammatory demyelinating polyneuropathy, and Guillain-Barre syndrome, as well as other autoimmune disorders.

PCT International Application Number PCT/US2007/008396 (WO 2007/117505) discloses that the anti-inflammatory activity of IVIG is a property of the Fc fragment and its linked glycan, requiring terminal α2,6 sialic acid linkages, indicating a combined requirement for the specific polypeptide backbone and glycan structure for immunosuppression. (see also Anthony, et al., 2008, *Science* 320: 373-376).

Nimmerjahn and Ravetch (2007, *J. Exp. Med.* 204: 11-15) review and disclose technology related to the use of high doses of IVIG for treating various immune disorders. The authors present several relevant models which might explain the means through which intravenous (IVIG) suppresses pathogenic inflammatory responses. To this end, a two cell model forwarded by the authors suggests that sialylated IgG interacts with a putative IgG receptor on a regulatory cell, such as a macrophage, which in turn would up-regulate expression of inhibitory FcγR expression on an effector macrophage. However, no specific receptor is identified.

It would be desirable to identify new compounds useful in treating inflammation associated with various immune disorders. Such methodology might be more plausible subsequent to identification of the receptor(s) which interact with and promote this IVIG-related anti-inflammatory activity. To this end, the present invention addresses and meets this need by identifying the receptor type which interacts with a sialylated IgG antibody or Fc fragment associated with IVIG therapy, thus allowing for methods and assays useful in identifying new drugs to complement or supplant existing IVIG-based treatment of autoimmune disorders.

SUMMARY OF THE INVENTION

The present invention relates in part to the identification of a receptor type which binds IgG antibodies or Fc fragments, thus inducing IVIG-related reversal of inflammation associated with various immune disorders. Such a receptor which binds IgG antibodies or Fc fragments, as disclosed herein, is a mammalian C-type lectin type known to bind intracellular adhesion molecule (ICAM)-3 (CD50), including but not limited to DC-SIGN (a human dendritic cell-specific adhesion receptor [CD209] found on dendritic cells), SIGN-R1 (the murine homologue of DC-SIGN, known to be expressed on splenic marginal zone macrophages), and related homologues and isoforms thereof. The identification of a "DC-SIGN receptor type" which interacts with IgG to promote a biological response reducing inflammation associated with immune disorders in turn provides a valuable and essential component when practicing additional aspects of the present invention, including but not necessarily limited to methods, uses and identified compositions for treating various immune disorders.

The present invention relates to methods of identifying modulators of a "DC-SIGN receptor type", a receptor type disclosed herein as interacting with IgG antibodies or Fc fragments to promote an anti-inflammatory effect associated with known IVIG treatment protocols. A modulator of particular interest is a compound which acts as an agonist to the DC-SIGN receptor type. While not being bound by theory, presumably such a compound will show the ability to mediate a signal from a DC-SIGN$^{(+)}$ cell (such as a dendritic cell) to an effector macrophage, causing an increase in expression of the FcγRIIB receptor, which in turn inhibits the cellular-mediated inflammatory response normally generated from these macrophages in response to relevant autoantibodies. The assay methods used to practice this portion of the invention may be any method currently available to the artisan, including but not limited to binding assays utilizing isolated DC-SIGN receptor type, isolated membrane fractions containing DC-SIGN receptor type, binding or cell-based activation assays utilizing DC-SIGN$^{(+)}$ cells, as well a functional sensor/effector cell assay measuring the ability of a test compound to stimulate a sensor cell (expressing a DC-SIGN receptor type) to mediate an up-regulation of the FcγRIIB receptor in an effector cell. While reference to a full length receptor is made throughout this specification, such a reference is not meant as a limitation. Instead, it is understood that such a full length receptor or a biologically relevant fragment of the receptor (such as a fragment at least comprising the "lectin domain" or "carbohydrate recognition domain" (herein after referred to as "lectin domain") may be utilized in practicing the methodology of the present invention. Thus, the present invention relates in part to methods of screening for compounds which (i) modulate (i.e., stimulate) activity of the DC-SIGN receptor type so as to promote an increase in expression of a measurable cellular component which may affect an increase in expression of the FcγRIIB receptor in a secondary macrophage; (ii) modulate the expression of DNA or RNA encoding a DC-SIGN receptor type protein; or (iii) stimulate a reporter gene linked to a downstream signaling pathway initiated by 2,6 Fc binding to a DC-SIGN receptor type. Thus, compounds may modulate by increasing or attenuating the expression of DNA or RNA encoding DC-SIGN receptor type, promote increased in vivo expression of the FcγRIIB receptor in a secondary effector macrophage, and/or by acting as an agonist or antagonist of the DC-SIGN receptor type receptor protein.

To this end, the present invention relates to a method of identifying a test compound which modulates a DC-SIGN receptor type cellular receptor so as to activate or suppress anti-inflammatory activity associated with autoantibody-mediated inflammation. Such a method comprises providing an amino acid sequence comprising at least the lectin domain of a DC-SIGN receptor type; contacting the DC-SIGN receptor type with a test compound; and measuring the extent of binding of the test compound to the receptor. A test compound shown to have measurable affinity to such a receptor (identified herein as a receptor involved in the process of intravenous IVIG modification of patient inflammation) is a candidate for further testing as a potential compound to use in treating various immune disorders.

The present invention also relates to a method of identifying a test compound which modulates a DC-SIGN receptor type so as to activate anti-inflammatory activity associated with autoantibody-mediated inflammation. Such a test compound will act as an agonist of a respective DC-SIGN receptor type. Thus, such methodology will comprise providing an amino acid sequence comprising a lectin domain of a DC-SIGN receptor type; contacting the DC-SIGN receptor type/lectin domain of the receptor with a test compound; and measuring the extent of binding of the test compound to the lectin domain. Again, any such test compound shown to have measurable affinity to such a DC-SIGN receptor type will be a candidate for additional testing as a compound to promote anti-inflammatory activity similar to intravenous IVIG-type products. Such methods of the present invention may be cell free high throughput methods. Such methods are particularly advantageous as a first-step screening methods demonstrating that the test compound is capable of binding the DC-SIGN receptor type/lectin domain or that the test compound affects binding of a control antibody to the DC-SIGN receptor type/lectin domain. Such assays will measure the binding of a test compound to the DC-SIGN receptor type (such as to the ligand binding domain) or, in other embodiments, the response of cells expressing DC-SIGN receptor type or functional fragments thereof. The methods of this portion of the invention are especially beneficial in identification of the candidate compounds which are useful as replacements of glycosylated polypeptides comprising an α2,6 Fc fragment, rather than potentiators of the anti-inflammatory activity of such polypeptides. In different embodiments, the presence or the amount of the complex between the candidate compound and the receptor/lectin domain is measured as described within this specification. In other embodiments, such as cell-based assays, the response of the cell expressing full length DC-SIGN receptor type or functional fragments thereof may also be measured.

The present invention further relates to a method of identifying a test compound which modulates a DC-SIGN receptor type so as to activate or suppress anti-inflammatory activity associated with IgG-mediated inflammation, wherein such a method comprises providing a first amino acid sequence comprising at least the lectin domain of a DC-SIGN receptor type; contacting the receptor with a control antibody or variant thereof and measuring the extent of binding of the control antibody to the receptor and/or relevant lectin domain in order to determine a baseline binding value. This baseline binding value can be used to compare to binding of a test compound which involves providing a second amino acid sequence comprising a DC-SIGN receptor type; contacting the receptor and/or relevant lectin domain from this second amino acid sequence with the test compound and measuring the extent of binding of the test compound to the receptor/lectin domain. Thus, the baseline binding value may then be compared to the extent of binding of the test compound.

The methods of the present invention may also be cell-based. If a cell-based assay is used, such techniques as, for example, cell sorting, may also be used to determine the amount of the complex of interest, such as, for example, the complex between the test compound and the DC-SIGN receptor type/lectin domain. Thus, assays described throughout this specification may utilize DC-SIGN$^{(+)}$ cells, which are (i) host cells transfected or transformed with an expression vector comprising a DC-SIGN receptor type or biologically relevant fragment (e.g., expressing the lectin domain or possibly an Fc-DC-SIGN receptor type fusion which expresses at least a portion of the extracellular domain which contains the lectin domain); (ii) a host cell line which has been genetically modified to overexpress host DC-SIGN receptor type, preferably resulting in at least a 5-fold increase over expression in a chosen "wild-type" host cell (such improvements of over-expression can be brought about by any means presently known in the art, including but not limited to introducing a promoter by homologous recombination while leaving the coding region intact), and/or (iii) host cells that for whatever biological reason express a high level of the DC-SIGN receptor type (e.g., including but not limited to dendritic cells). Additionally, the methods described herein may be modified such that the assay of interest is carried out in the presence of membrane preparations from DC-SIGN$^{(+)}$ cells, or alternatively, a DC-SIGN receptor type (or biologically relevant fragment) may be utilized to screen test compounds which show affinity for the receptor.

Test compounds identified by the methods described herein preferably act as an agonist of the DC-SIGN receptor-type and may be an antibody, an antibody fragment (such as an Fc fragment), a peptide, a protein, a non-proteinaceous organic molecule, ribozyme, and/or anti-sense molecule, any of which may be useful in promoting anti-inflammatory activity associated with intravenous IVIG-based treatment.

The present invention relates in part to a compound which acts to modulate a DC-SIGN receptor type (e.g., such as an agonist of the receptor), such that the compound modulates the DC-SIGN receptor type so as to mediate a therapeutically effective signal from a DC-SIGN$^{(+)}$ cell to an effector macrophage, causing an increase in expression of the FcγRIIB receptor, which in turn inhibits the cellular-mediated inflammatory response normally generated from these macrophages in response to relevant autoantibodies. To this end, the present invention further relates to a pharmaceutical composition which comprises such a compound in combination with at least one pharmaceutically effective excipient, such that this pharmaceutical composition is present in a therapeutically effective concentration for administration to a mammal, including but not limited to humans.

The present invention also relates to methods of treating one or more immune disorders, as disclosed herein, through administration to a mammalian host (including but not limited to a human) of a modulator (such as a DC-SIGN receptor type agonist) which activates a DC-SIGN receptor type (such as human DC-SIGN receptor). Such a DC-SIGN receptor type agonist may be identified through the methods described herein and will be useful in treating immune disorders, including but not limited to immune thrombocytopenia (ITP), autoimmune hemolytic anemia (AHA), systemic lupus erythematosus (SLE), Kawsaki's disease (an acute vasculitic syndrome), sclerodema, rheumatoid arthritis (RA), chronic inflammatory demylinating polyneuropathy (CIDP), pemphigus and other conditions associated with autoantibody mediated inflammation.

DETAILED DESCRIPTION OF THE INVENTION

Figure 1:
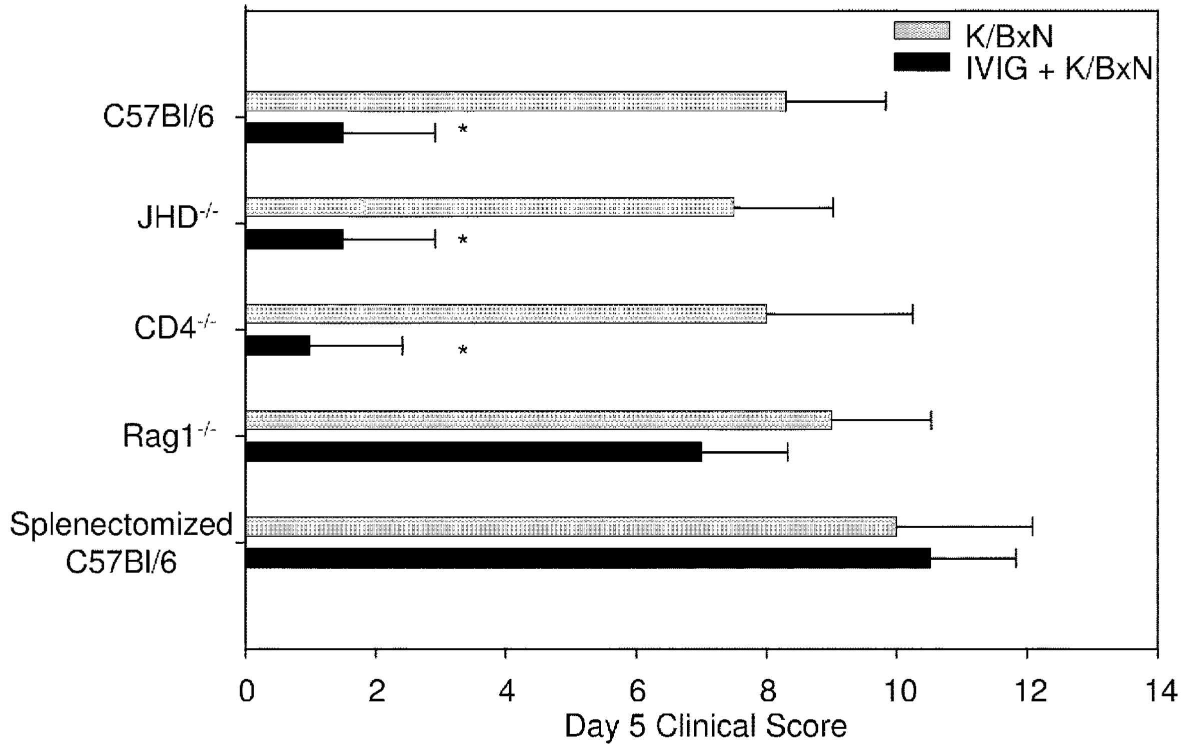
FIG. 1 shows that a non-B, non-T splenic population is targeted by IVIG.

The methods of the present invention are based partly on the identification herein of a receptor type which binds an IgG antibody or fragment known to promote IVIG-based treatment of immune disorders. Such a receptor is a mammalian C-type lectin receptor type known to bind intracellular adhesion molecule (ICAM)-3 (CD50), including but not limited to DC-SIGN (a human dendritic cell-specific adhesion receptor [CD209] found on dendritic cells), SIGN-R1 (the murine homologue of DC-SIGN, known to be expressed on splenic marginal zone macrophages), as well as any relevant mammalian homologues or isoforms thereof. The human DC-SIGN receptor, identified by Geijtenbeek, et al (2000, Cell 100: 575-585; see also U.S. Pat. No. 6,391,507) is a C-type lectin (calcium dependent) receptor which is expressed at least on dendritic cells, macrophages and activated B cells. This receptor is functional as a tetramer and comprises a carbohydrate recognition domain (CRD), a repeat domain, a transmembrane domain and a intracellular cytoplasmic domain, containing 3 internalization motifs (for a review, see Wu and KewalRamani, 2006, *Nat. Immunol.* 6(11): 859-868). It has been documented that the DC-SIGN receptor binds a variety of viral, bacterial, fungal and parasitic pathogens, including but not limited to human immunodeficiency virus ("HIV," e.g., see U.S. Pat. No. 6,391,567, Garcia et al., 2005, *Traffic* 6: 488-501; Hodges et al., 2007, Nat. Immunol. 8 (6):569-577), hepatitis C virus ("HCV," e.g., see U.S. Pat. No.

7,022,323), *Mycobacterium bovis* (EP 1 407 965 A1), Ebolavirus (Marzi et al., 2006, *J. Virol.* 80 (13): 6305-6317), Measles virus (Lot de Witte et al., *J. Virol.* 80 (7): 3477-3486), and Dengue virus (WO 2004/041299). To this end, it has been suggested that this C-type lectin receptor may be a target for a compound that may modulate the receptor, such as mannose, fucose, plant lectins, antibiotics, sugars, proteins or antibodies raised against the receptor (see, e.g., U.S. Pat. No. 7,148,329). To the best of the inventors knowledge, there has been no previous disclosure directly linking a DC-SIGN receptor type to the therapeutic value obtained in treating autoimmune disorders via an IVIG-based treatment strategy. Thus, as described further herein, the present invention relates in part to methods of screening for and selecting compounds which modulate (and preferably act as an agonist) of a DC-SIGN receptor type in order to promote a similar anti-inflammatory response as has been historically shown with IVIG administration. Therefore, the identification of this receptor type (which is disclosed herein to interact with IgG to activate a biological response promoting an anti-inflammatory state in various autoimmune disorders) provides a valuable and essential component allowing for screening and selection of additional compounds which may be useful in treating various immune disorders which to date have been amenable to treatment through IVIG-based techniques.

To this end, the present invention relates in part to methods of identifying modulators of the function of the DC-SIGN receptor type. Such methods may entail any assay available to the artisan, from screening of large libraries of candidate test compounds, to assays which may focus on a related subset or class of compounds (such as antibodies or related Fc fragments), to assays focusing on specific structural attributes which may provide for selection of an enhanced Fc antibody fragment (such as an α2,6 sialyated Fc fragment) more likely to modulate the function of the DC-SIGN receptor type, thus mediating a signaling pathway to promote increased in vivo expression of the FcγRIIB receptor. The various assays which may be utilized to identify compounds which modulate a DC-SIGN receptor type (i.e., through binding and/or modulation of the receptor via interaction with at least portion of the amino acid sequence of the DC-SIGN receptor type) include but are not limited to assays conducted in cell free systems (such as an isolated DC-SIGN receptor, a fusion construct containing a lectin domain [e.g., and Fc-LBD fusion construct], or a fragment containing a lectin domain), or conducted with one or more isolated cell types (in either binding or functional assays), or with associated membrane fractions, in organisms (such as transgenic animals), or a combination thereof. Such assays may identify a developmental candidate compound which shows both an affinity for the DC-SIGN receptor type, and especially a compound which activates the DC-SIGN receptor type so as to affect an increase in expression of the FcγRIIB receptor in a secondary effector cell. A modulator (such as a compound which activates a DC-SIGN receptor type to induce signaling of an effector cell to increase expression of the FcγRIIB receptor in a secondary effector cell) may be a compound which alters the function of the target receptor, as determined by binding and/or function of the receptor in the presence and/or absence of a test compound.

Any polynucleotide sequence which encodes a functional DC-SIGN receptor type (or at least a biologically effective binding domain from the respective receptor) so as to affect proper expression of the biologically relevant amino acid sequence of the respective DC-SIGN receptor type may be utilized in the recombinant cell and membrane-based assays discussed herein. As examples, but in no way presented as a limitation, polynucleotides which may be utilized in constructing an appropriate DNA expression vector is a DNA molecule which comprises the open reading frame for a mammalian DC-SIGN receptor type, such as a polynucleotide sequence as set forth in SEQ ID NO:1 (DC-SIGN; Accession No. NM_021155, with an open reading from nucleotide 10-1224, encoding human DC-SIGN receptor [see SEQ ID NO:2]) and SEQ ID NO:3 (SIGNR1; Accession No. SF3733409, with an open reading from nucleotide 28-1005, encoding murine SIGNR-1 receptor [see SEQ ID NO:4]), as well as various homologues, splice variants and/or isoforms, such as disclosed in US 2005/0221291 A1 (Ahuha et al).

Assays described throughout this specification may utilize DC-SIGN$^{(+)}$ cells which are (i) host cells transfected or transformed with an expression vector comprising a DC-SIGN receptor type or biologically relevant fragment (e.g., expressing the lectin domain or possibly an Fc-DC-SIGN receptor type fusion which expresses at least a portion of the extracellular domain which contains the lectin domain); (ii) a host cell line which has been genetically modified to overexpress host DC-SIGN receptor type, preferably resulting in at least a 5-fold increase over expression in a chosen "wild-type" host cell (such improvements of overexpression can be brought about by any means presently known in the art, including but not limited to introducing a promoter by homologous recombination while leaving the coding region intact), and (iii) host cells that for whatever biological reason express a high level of the DC-SIGN receptor type (e.g., including but not limited to dendritic cells) may be utilized to screen and/or select for modulators useful in the treatment various immune disorders presently amenable to treatment via IVIG administration. Thus, any such cell of (i), (ii), (iii), or any other cell type which shows biologically relevant amount of DC-SIGN receptor type may be designated herein as a "DC-SIGN$^{(+)}$ cell" and may be useful in one or more of the methods disclosed herein. As described further herein, the present invention relates in part to cell- and membrane-based methods of identifying selective agonists and/or antagonists of mammalian DC-SIGN receptor types. A specific object of the present invention provides for DC-SIGN receptor type-based assays to screen for selective agonists of this receptor protein which regulate in vivo expression of the FcγRIIB receptor in an effector cell. Again, these assays may be cell-based assays; whereby a DNA molecule encoding a DC-SIGN receptor type is transfected or transformed into a host cell and this recombinant host cell is allowed to grow for a time sufficient to express the DC-SIGN receptor. Alternatively, any "non-recombinant" cell line which is DC-SIGN$^{(+)}$ may also be utilized to screen and/or select for modulators of DC-SIGN useful in the treatment of various immune disorders. In addition, substantially purified membrane fractions from such a DC-SIGN$^{(+)}$ cell may be used in an assay to screen and/or select for modulators of a mammalian DC-SIGN receptor type associated with promoting an in vivo anti-inflammatory affect through up-regulation of the FcγRIIB receptor in a secondary effector cell).

Any such polynucleotide as mentioned above or a biologically equivalent polynucleotide available to the artisan for the same intended purpose may be inserted into an appropriate expression vector and linked with other DNA molecules, i.e., DNA molecules to which the DC-SIGN receptor type are not naturally linked, to form "recombinant DNA molecules" expressing this receptor. These vectors may be comprised of DNA or RNA; for most cloning purposes DNA vectors are preferred. Typical vectors include plasmids, modified viruses, bacteriophage and cosmids, yeast artificial chromosomes and other forms of episomal or integrated DNA that can encode a DC-SIGN receptor type. It is well within the purview of the artisan to determine an appropriate vector for a particular use.

A variety of mammalian expression vectors may be used to express recombinant DC-SIGN receptor type in mammalian cells. As noted above, expression vectors are defined herein as DNA sequences that are required for the transcription of cloned DNA and the translation of their mRNAs in an appropriate host. Such vectors can be used to express eukaryotic DNA in a variety of hosts such as bacteria, blue green algae, plant cells, insect cells and animal cells. Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses. Commercially available mammalian expression vectors which may be suitable for recombinant DC-SIGN receptor type expression, include but are not limited to, pcDNA3.neo (Invitrogen), pcDNA3.1 (Invitrogen), pCI-neo (Promega), pLITMUS28, pLITMUS29, pLITMUS38 and pLITMUS39 (New England Bioloabs), pcDNAI, pcDNAIamp (Invitrogen), pcDNA3 (Invitrogen), pMClneo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and IZD35 (ATCC 37565).

Also, a variety of bacterial expression vectors may be used to express recombinant DC-SIGN receptor type in bacterial cells. Commercially available bacterial expression vectors which may be suitable for recombinant DC-SIGN receptor type expression include, but are not limited to pCR2.1 (Invitrogen), pET11a (Novagen), lambda gt11 (Invitrogen), and pKK223-3 (Pharmacia). In addition, a variety of fungal cell expression vectors may be used to express recombinant DC-SIGN receptor type in fungal cells. Commercially available fungal cell expression vectors which may be suitable for recombinant DC-SIGN receptor type expression include but are not limited to pYES2 (Invitrogen) and *Pichia* expression vector (Invitrogen). Also, a variety of insect cell expression vectors may be used to express recombinant receptor in insect cells. Commercially available insect cell expression vectors which may be suitable for recombinant expression of DC-SIGN receptor type include but are not limited to pBlueBacIII and pBlueBacHis2 (Invitrogen), and pAcG2T (Pharmingen).

To determine the DC-SIGN receptor type cDNA sequence(s) that yields optimal levels of DC-SIGN receptor type, cDNA molecules including but not limited to the following can be constructed: a cDNA fragment containing the full-length open reading frame for DC-SIGN receptor type as well as various constructs containing portions of the cDNA encoding only specific domains of the protein or rearranged domains of the protein, including but not limited to a portion of the cDNA encoding at least the lectin domain of a DC-SIGN receptor type (e.g., an Fc-LBD fusion construct). All constructs can be designed to contain none, all or portions of the 5' and/or 3' untranslated region of a DC-SIGN receptor type. The expression levels and activity of DC-SIGN receptor type can be determined following the introduction of these constructs into appropriate host cells. Following determination of the DC-SIGN receptor type cassette yielding optimal expression in transient assays, this DC-SIGN receptor type cDNA construct is transferred to a variety of expression vectors (including recombinant viruses), including but not limited to those for mammalian cells, plant cells, insect cells, oocytes, bacteria, and yeast cells.

The host cells engineered to contain and/or express DNA sequences encoding the DC-SIGN receptor type can be cultured under suitable conditions to produce DC-SIGN receptor type or a biologically equivalent form. These recombinant host DC-SIGN$^{(+)}$ cells may be prokaryotic or eukaryotic, including but not limited to, bacteria such as *E. coli*, fungal cells such as yeast, mammalian cells including, but not limited to, cell lines of human, bovine, porcine, monkey and rodent origin, and insect cells including but not limited to *Drosophila* and silkworm derived cell lines. For instance, one insect expression system utilizes *Spodoptera frugiperda* (Sf21) insect cells (Invitrogen) in tandem with a baculovirus expression vector (pAcG2T, Pharmingen). Also, mammalian cells lines which may be suitable and which are commercially available, include but are not limited to, L cells L-M(TK$^-$) (ATCC CCL 1.3), L cells L-M (ATCC CCL 1.2), Saos-2 (ATCC HTB-85), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171), CPAE (ATCC CCL 209), and HOS cells (human osteogenic sarcoma; ATCC CRL 1543). The expression vector may be introduced into host cells via any one of a number of techniques including but not limited to transformation, transfection, protoplast fusion, and electroporation. Transformation is meant encompass a genetic change to the target cell resulting from an incorporation of DNA. Transfection is meant to include any method known in the art for introducing DC-SIGN receptor type into the test cells. For example, transfection includes calcium phosphate or calcium chloride mediated transfection, lipofection, infection with a retroviral construct containing DC-SIGN receptor type, and electroporation. The expression vector-containing cells are individually analyzed to determine whether they produce DC-SIGN receptor type protein. Identification of DC-SIGN receptor type expressing cells may be done by several means, including but not limited to immunological reactivity with anti-DC-SIGN receptor type antibodies, labeled lectin binding and the presence of host cell-associated DC-SIGN receptor type activity. Host cells that may be particularly useful in practicing these methods of the present invention additionally include, but are in no way limited to, MARCO$^{(+)}$ marginal zone macrophages.

Thus, the specificity of binding of compounds showing affinity for DC-SIGN receptor type is shown by measuring the affinity of the compounds for cells expressing the DC-SIGN receptor type, membrane preparations from such cells, or the receptor (or at least a portion containing the lectin domain; such as an Fc-LBD fusion construct), which can be immobilized for screening purposes. Expression of the cloned receptor and screening for compounds that bind to a DC-SIGN receptor type or that inhibit the binding of a known ligand of DC-SIGN receptor type (such as an Fc fragment containing a $\alpha$2,6-linked sialic acid) to these cells, or membranes prepared from these cells, provides an effective method for the rapid selection of compounds with high affinity for DC-SIGN receptor type which may be useful in the treating various immune disorders. Such ligands need not necessarily be labeled but can also be nonisotopic compounds that can be used to displace bound labeled compounds or that can be used as activators in functional assays. Compounds identified by the methods described herein are likely to be agonists or antagonists of DC-SIGN receptor type and, as mentioned herein, may be antibodies, antibody fragments (such as Fc fragments and/or Fc fragments containing a α2,6-linked sialic acid), other types of peptides, proteins, as well as non-proteinaceous organic molecules, all of which may be useful in the treatment of various immune disorders, and at least such immune disorders which are amenable to treatment via IVIG techniques.

The present invention relates in part to methods of screening for compounds which (i) modulate (i.e., stimulate) activity of the DC-SIGN receptor type so as to promote an increase in expression of a measurable cellular component which may affect an increase in expression of the FcγRIIB receptor in a secondary macrophage; or (ii) modulate the expression of DNA or RNA encoding a DC-SIGN receptor type protein (iii) stimulate a reporter gene linked to a downstream signaling pathway initiated by 2,6 Fc binding to a DC-SIGN receptor type. Thus, compounds may modulate by increasing or attenuating the expression of DNA or RNA encoding DC-SIGN receptor type, promote increased in vivo expression of the FcγRIIB receptor in a secondary effector macrophage, and/or by acting as an agonist or antagonist of the DC-SIGN receptor type receptor protein. These compounds that modulate the expression of DNA or RNA encoding DC-SIGN receptor type or the biological function of the receptor thereof may be detected by a variety of assays. The assay may be a simple "yes/no" assay to determine whether there is a change in expression or function. The assay may be made quantitative by comparing the expression or function of a test sample with the levels of expression or function in a standard sample. Kits containing DC-SIGN receptor type, antibodies to DC-SIGN receptor type, or modified DC-SIGN receptor type may be prepared by known methods for such uses. Methods for identifying agonists and antagonists of other receptors are well known in the art and can be adapted to identify agonists and antagonists of DC-SIGN receptor type. For example, Cascieri et al. (1992, *Molec. Pharmacol.* 41:1096-1099) describe a method for identifying test compounds that inhibit agonist binding to rat neurokinin receptors and thus are potential agonists or antagonists of neurokinin receptors. The method involves transfecting COS cells with expression vectors containing rat neurokinin receptors, allowing the transfected cells to grow for a time sufficient to allow the neurokinin receptors to be expressed, harvesting the transfected cells and resuspending the cells in assay buffer containing a known radioactively labeled agonist of the neurokinin receptors either in the presence or the absence of the test compound, and then measuring the binding of the radioactively labeled known agonist of the neurokinin receptor to the neurokinin receptor. If the amount of binding of the known agonist is less in the presence of the test compound than in the absence of the test compound, then the test compound is a potential agonist or antagonist of the neurokinin receptor. Where binding of the test compound such as an agonist or antagonist to DC-SIGN receptor type is measured, such binding can be measured by employing a labeled test compound or agonist. The test compound or agonist can be labeled in any convenient manner known to the art, e.g., fluorescently, enzymatically, radioactively. When screening for a modulator that antagonizes the target receptor (such as DC-SIGN receptor type) a cell-based assay may rely on the inclusion of a known ligand (such as an Fc fragment containing a α2,6-linked sialic acid) in combination with the test compound so as to measure the functional ability of the test compound to agonize or antagonize receptor activity. Therefore, the specificity of binding of compounds having affinity for DC-SIGN receptor type is shown by measuring the affinity of the compounds for this receptor on DC-SIGN$^{(+)}$ cells. The use of DC-SIGN$^{(+)}$ cells to screen for compounds that bind to DC-SIGN receptor type or that inhibit the binding of a known, labeled ligand of DC-SIGN receptor type to these cells, or membranes prepared from these cells, provides an effective method for the rapid selection of compounds with high affinity for DC-SIGN receptor type. However, such ligands need not necessarily be labeled but can also be compounds that can be used to displace bound labeled compounds or that can be used as activators in functional assays. Compounds identified by the above method are likely to be agonists or antagonists of DC-SIGN receptor type and, again, may be antibodies, antibody fragments such as Fc fragments, peptides, proteins, or non-proteinaceous organic molecules which may be useful for human administration to treat various immune-related maladies, including but in no way limited to autoimmune diseases such as immune thrombocytopenia (ITP), autoimmune hemolytic anemia (AHA), systemic lupus erythematosus (SLE), Kawsaki's disease (an acute vasculitic syndrome), sclerodema, rheumatoid arthritis (RA), chronic inflammatory demylinating polyneutrophaty (CIPD), phemigus and other conditions associated with autoantibody mediated inflammation.

At one level, methods described herein entail providing an amino acid sequence comprising at least the lectin domain of a DC-SIGN receptor type (and up to and including the full length DC-SIGN receptor type); contacting the receptor/binding domain of the receptor with a test compound; and measuring the extent of binding of the test compound to the receptor/binding domain. A test compound shown to have measurable affinity to the receptor/binding domain is a candidate for further testing as an modulator (i.e., agonist or antagonist) of the DC-SIGN receptor type, and thus a potential compound to at least treat various autoimmune disorders previously shown to be amenable to treatment through intravenous IVIG.

Another related aspect of this portion of the invention involves a method of identifying a test compound which modulates a DC-SIGN receptor type which comprises providing a first amino acid sequence comprising a biologically relevant binding domain of a DC-SIGN receptor type (including but not limited to the lectin domain) selected from a DC-SIGN receptor type, contacting the receptor/binding domain with a control antibody (e.g., such as a Fc fragment containing a α2,6-linked sialic acid) or variant thereof and measuring the extent of binding of the control antibody to the receptor/binding domain in order to determine a baseline binding value. This baseline binding value can be used to compare to binding of a test compound which involves providing a second amino acid sequence selected from a DC-SIGN receptor type or fragment thereof; contacting the receptor/binding domain from this second amino acid sequence with the test compound and measuring the extent of binding of the test compound to the receptor/binding domain. Thus, the baseline binding value may then be compared to the extent of binding of the test compound.

Another embodiment of the present invention relates in part to methods of identifying a test compound which modulates DC-SIGN receptor type receptor activity, which involves:

(a) combining a test compound in the presence and absence of a DC-SIGN receptor type protein, including but not limited to a DC-SIGN receptor type protein comprising an amino acid sequence as set forth in SEQ ID NO:2 and SEQ ID NO:4; and, (b) measuring and comparing the effect of the test compound in the presence and absence of the DC-SIGN receptor type receptor protein.

Several additional embodiments are disclosed herein to show, but in now way limit, the diverse type of screening or selection assay which the skilled artisan may utilize in tandem with an expression vector directing the expression of the DC-SIGN receptor type receptor protein. Again, methods for identifying agonists and antagonists of other receptors are well known in the art and can be adapted to identify agonists and antagonists of a DC-SIGN receptor type. Therefore, these embodiments are presented as examples and not as limitations. To this end, the present invention includes assays by which DC-SIGN receptor type modulators (such as agonists, inverse agonists and antagonists) may be identified. Accordingly, one embodiment of the present invention includes a method for determining whether a test compound is a potential agonist of a DC-SIGN receptor type, and thus useful in the treating an immune disorder by acting to promote an host anti-inflammatory response, comprising:

(a) transfecting or transforming cells with an expression vector that directs expression of DC-SIGN receptor type in the cells, resulting in DC-SIGN$^{(+)}$ cells;

(b) allowing the DC-SIGN$^{(+)}$ cells to grow for a time sufficient to allow DC-SIGN receptor type to be expressed;

(c) exposing the DC-SIGN$^{(+)}$ cells to a labeled ligand (including but not limited to a control antibody known to promote an anti-inflammatory response in vivo) of a DC-SIGN receptor type in the presence and in the absence of the test compound; and, (d) measuring the binding of the labeled ligand to a DC-SIGN receptor type; where if the amount of binding of the labeled ligand is less in the presence of the test compound than in the absence of the test compound, then the test compound is a potential agonist of the DC-SIGN receptor type.

Any type of DC-SIGN$^{(+)}$ cell (and not just recombinant DC-SIGN$^{(+)}$ cells) may be utilized in step (a) and (b) of such a binding assay when screening test compounds for possible development candidates which have the ability to activate the DC-SIGN receptor type. As noted herein, a preferred 'non-recombinant' DC-SIGN$^{(+)}$ cell may be a dendritic cell which has been cultured under conditions which stimulate DC-SIGN expression (e.g., see Hodges, et al., 2007*, Nature Immunology* 8 (6): 569-570). Also, the conditions under which step (c) of the method is practiced are conditions that are typically used in the art for the study of protein-ligand interactions: e.g., physiological pH; salt conditions such as those represented by such commonly used buffers as PBS or in tissue culture media; a temperature of about 4° C. to about 55° C., as well as an adequate concentration of calcium, known to affect the activity of a C-type lectin receptor such as a DC-SIGN receptor type. The test cells may be harvested and resuspended in the presence of the test compound and the labeled ligand. In a modification of the above-described method, step (c) is modified in that the cells are not harvested and resuspended but rather the labeled known agonist (such as a Fc fragment containing a $\alpha$2,6-linked sialic acid) and the test compound are contacted with the cells while the cells are attached to a substratum, e.g., tissue culture plates.

The present invention also includes a method for determining whether a test compound is capable of binding to a DC-SIGN receptor type, or relevant extracellular domain, or a relevant mutant DC-SIGN receptor type that is no longer functional but nonetheless may be involved in lectin binding, i.e., whether the test compound is a potential agonist, inverse agonist or an antagonist of DC-SIGN receptor type, where the method comprises:

(a) transfecting or transforming cells with an expression vector that directs the expression of DC-SIGN receptor type in the cells, resulting in DC-SIGN$^{(+)}$ cells;

(b) exposing the DC-SIGN$^{(+)}$ cells to the test compound;

(c) measuring the amount of binding of the test compound to DC-SIGN receptor type; and, (d) comparing the amount of binding of the test compound to DC-SIGN receptor type in the DC-SIGN$^{(+)}$ cells with the amount of binding of the test compound to control cells (i.e., DC-SIGN$^{(-)}$ cells) that have not been transfected with DC-SIGN receptor type or which are known to have substantially less DC-SIGN$^{(+)}$ receptor than, say, a dendritic cell;

wherein if the amount of binding of the test compound is greater in the DC-SIGN$^{(+)}$ cell (i.e., test cells) as compared to the control cells, the test compound is capable of binding to DC-SIGN receptor type. Determining whether the test compound is actually an agonist or antagonist can then be accomplished by the use of a functional assay.

Again, any type of DC-SIGN$^{(+)}$ cell may be utilized in such a binding assay when screening test compounds for possible development candidates which have the ability to activate the DC-SIGN receptor type. Thus, in the methods described herein, 'recombinant' DC-SIGN$^{(+)}$ cells of step (a) may be substituted with 'non-recombinant' DC-SIGN$^{(+)}$ cells, including but not limited to dendritic cells. The conditions under which step (b) of the method is practiced are conditions that are typically used in the art for the study of protein-ligand interactions: e.g., physiological pH; salt conditions such as those represented by such commonly used buffers as PBS or in tissue culture media; a temperature of about 4° C. to about 55° C., as well as an adequate concentration of calcium, known to affect the activity of a C-type lectin receptor such as a DC-SIGN receptor type. The test cells are normally harvested and then resuspended in the presence of the test compound.

Such cellular-based methodologies as disclosed herein and further known to the artisan are also amenable to be set up as functional assays, where a response of the cell is measured. If the user of the method chooses to measure the response of the cell, it is beneficial if the cell expresses a full length DC-SIGN receptor type, or functional fragments of these molecules. Generally, the functional fragments include not only lectin domains, but also transmembrane domains and signal transduction domains of a DC-SIGN receptor type. To this end, another aspect of the present invention relates to methods of screening and selecting for test compounds capable of binding and modulating a DC-SIGN receptor type. Of special interest are assays which effectively measure the ability of a test compound to activate the DC-SIGN receptor type (i.e., to act as an agonist of the receptor). Such functional assays will be useful alone or in combination with other methodologies (e.g., binding assays, transgenic animal model studies, etc.) in order to identify test compounds which are candidates (or which may represent a candidate class of compounds) targeted for development. Therefore, it will be evident to the artisan that a functional assay may be contemplated which provides for an quantitative and/or qualitative determination of receptor modulation of a DC-SIGN. For example, Caparrós et al. (2006, *Blood* 107 (10): 3950-3958) disclose that antibody-mediated stimulation of the human DC-SIGN receptor in both activated dendritic cells and cells transfected with a human DC-SIGN expression vector activate of MAP kinases Erk1 and Erk2, phospatidylinositol-3-OH kinase (PI3K), increasing interleukin-10 (IL-10), as well as transiently increasing intracellular calcium. Also, Hodges et al (2007, *Nature Immunology* 8 (6): 569-570) disclose that activation of the DC-SIGN receptor results in the down-regulation (MHC II, Jagged 1 and interferon-response transcripts) and up-regulation (the transcription factor, ATF3) of specific dendritic cell genes. To this end, the present invention further relates to methods of identifying test compounds which modulate a DC-SIGN receptor type so as to activate or suppress anti-inflammatory activity associated with various immune disorders which may be amenable to known IVIG-based treatment, such methods comprising:

(a) providing DC-SIGN$^{(+)}$ cells, such as dendritic cells or cells transfected or transduced with an expression vector encoding a DC-SIGN receptor type;

(b) exposing the DC-SIGN$^{(+)}$ cells to a test compound; and, (c) measuring the increase or decrease in a cellular component within the DC-SIGN$^{(+)}$ cells, wherein an increase in the level of a cellular component (such as Erk1 and/or Erk2, PI3K, IL-10, intracellular calcium, ATF3 or a decrease in mRNA transcripts related to MHC II components, Jagged 1 and/or interferon-response transcripts) as compared to the level of that respective cellular component(s) in cells not contacted by the test compound (or DC-SIGN$^{(-)}$ cells also exposed to the test compound) indicates that the test compound is an agonist of the respective DC-SIGN receptor type. The DC-SIGN$^{(+)}$ cells may be cultured for a sufficient time in the appropriate buffer system to allow expression of the DC-SIGN receptor type and may optionally be harvested and resuspended in an appropriate buffer, as described herein and/or as known in the art, prior to exposing DC-SIGN$^{(+)}$ cells to a test compound.

These type of functional assays may also be based on measurement of induction and expression of a reporter gene or epitope tag within a recombinant DC-SIGN$^{(+)}$ cell. The art is now replete with various reporter genes and epitope tag polypeptides available to the artisan that will be suitable to measuring the ability of a test compound to modulate a DC-SIGN receptor type. The artisan will be capable of mixing and matching these various research tools without undue experimentation. For example, various reporter genes include but are not limited to green fluorescent protein ("GFP") or functional protein/polypeptide derivatives thereof. GFP genes and various mutants (which may fluoresce at different wavelengths and improved spectal properties) have been identified in a variety of organisms in the phyla hydrozoa, cnidaria, anthozoa and ctenophora. Select GFP variants include blue fluorescent protein ("BPF"), yellow fluorescent protein (YFP), and cyan fluorescent protein (CFP). For additional suitable fluorescent proteins, see Matz et al., 1999, *Nature Biotechnology* 17:969-973. Other suitable reporter genes include chloramphenicol acetyl transferase ("CAT") and other enzyme detection systems, such as beta-galactosidase (β-gal"); firefly luciferase, bacterial luciferase, or secreted alkaline phosphate ("SEAP"). Other examples of suitable reporter genes include those which encode proteins conferring drug/antibiotic resistance to the host mammalian cell. The amount of transcription from the reporter gene may be measured using any suitable method known in the art, including detecting RNA expression via Northern blots, protein expression by any detection method known to that protein, such as a characteristic stain or an intrinsic activity (e.g., such as enzyme activity, or giving rise to a detection signal based on fluorescence, color, or luminescence, as discussed above). It is also possible that the activated reporter gene will provide an expressed protein which provides a growth advantage for the cell (e.g., be enhancing cell viability, relieving a cell nutritional requirement, and/or providing drug resistance). Other reporter genes may encode cell surface proteins for which antibodies or ligands are available. Expression of the reporter gene allows cells to be detected or affinity purified by the presence of the surface protein. Alternatively, the fused polypeptide is an epitope tag, examples of which include but are not limited to a Myc tag, a Flag tag, a His tag, a Leucine tag, an IgG tag, a biotinylation sequence site ("BSS," i.e., a streptavidin tag) and the like.

Thus, as discussed above, such gene reporter assays are well known in the art and can be adapted by the artisan to measure the quantitative and/or qualitative effect of signaling of a DC-SIGN receptor type by a test compound in a similar fashion as a control antibody (such as a α2,6 Fc) modulates a DC-SIGN receptor type. For example, Chen et al. (1995, *Analytical Biochemistry* 226: 349-354) describe a calorimetric assay which utilizes a recombinant cell transfected with an expression vector encoding a G-protein coupled receptor with a second expression vector containing a promoter with a cAMP responsive element fused to the LacZ gene. Activity of the overexpressed G-protein coupled receptor is measured as the expression and OD measurement of β-Gal.

Therefore, another aspect of this portion of the invention includes a non-radioactive method for determining whether a test compound modulates a DC-SIGN receptor type. Any downstream signal from DC-SIGN modulation may substance is a potential agonist or antagonist of MC-3R that comprises:

(a) transfecting or transforming cells with an expression vector encoding a DC-SIGN receptor type, resulting in recombinant DC-SIGN$^{(+)}$ cells;

(b) transfecting or transforming the test cells of step (a) with an expression vector which comprises a promoter fused to a reporter gene;

(c) harvesting the transfected cells and resuspending the cells in the presence of a known agonist of a DC-SIGN receptor type (such as a control antibody) in both the presence and absence of the test compound; and, (d) measuring the binding of the known agonist and test compound to overexpressed MC-3R by an assay which measures expression of the reporter gene off the promoter sequence and comparing expression levels in the presence of the known agonist as well as in the presence and absence of the test compound to determine whether the test compound acts as either a potential agonist or antagonist of the DC-SIGN receptor type.

Step (a) may also utilize a non-recombinant DC-SIGN$^{(+)}$ cell. Also, once standard controls are set, it is possible to perform such assays without the use of a control antibody or other control compound, since measurable increases in expression of a reporter gene will correlate to the effect that signaling molecule is known to possess in that DC-SIGN$^{(+)}$ cell; including but not limited to an increase in the level of a cellular component (such as Erk1 and/or Erk2, PI3K, IL-10, intracellular calcium, ATF3 or a decrease in mRNA transcripts related to MHC II components, Jagged 1 and/or interferon-response transcripts) as seen by modulation of human DC-SIGN, as discusses above.

The above-described methods can be modified in that, rather than exposing the DC-SIGN$^{(+)}$ cells (i.e., test cells) to the test compound, membranes can be prepared from the test cells and those membranes can be exposed to the test compound. Such a modification utilizing membranes rather than cells is well known in the art and is described in, e.g., Hess et al., 1992, *Biochem. Biophys. Res. Comm.* 184: 260-268. Accordingly, another embodiment of the present invention includes a method for determining whether a test compound binds and/or is a potential agonist or antagonist of DC-SIGN receptor type wherein membrane preparations from the DC-SIGN$^{(+)}$ cells are utilized in place of the whole DC-SIGN$^{(+)}$ cells. Such methods comprise the following and may utilized the physiological conditions as noted above:

(a) providing DC-SIGN$^{(+)}$ cells, such as dendritic cells or cells transfected or transduced with an expression vector encoding a DC-SIGN receptor type;

(b) preparing membranes containing DC-SIGN receptor type from the DC-SIGN$^{(+)}$ cells and exposing the membranes to a ligand of DC-SIGN receptor type under conditions such that the ligand binds to the DC-SIGN receptor type in the membranes;

(c) subsequently or concurrently to step (b), exposing the membranes from the DC-SIGN$^{(+)}$ cells to a test compound;

(d) measuring the amount of binding of the ligand to the DC-SIGN receptor type in the membranes in the presence and the absence of the test compound; and, (e) comparing the amount of binding of the ligand to DC-SIGN receptor type in the membranes in the presence and the absence of the test compound where a decrease in the amount of binding of the ligand to DC-SIGN receptor type in the membranes in the presence of the test compound indicates that the test compound is capable of binding to DC-SIGN receptor type.

The present invention also relates to a method for determining whether a test compound is capable of binding to DC-SIGN receptor type comprising:

(a) providing DC-SIGN$^{(+)}$ cells, such as dendritic cells or cells transfected or transduced with an expression vector encoding a DC-SIGN receptor type;

(b) preparing membranes containing DC-SIGN receptor type from the test cells and exposing the membranes from the test cells to the test compound;

(c) measuring the amount of binding of the test compound to the DC-SIGN receptor type in the membranes from the test cells; and, (d) comparing the amount of binding of the test compound to DC-SIGN receptor type in the membranes from the test cells with the amount of binding of the test compound to membranes from control cells (e.g., DC-SIGN$^{(-)}$ cells), where if the amount of binding of the test compound to DC-SIGN receptor type in the membranes from the test cells is greater than the amount of binding of the test compound to the membranes from the control cells, then the test compound is capable of binding to DC-SIGN receptor type.

Another method for selecting a test compound which may be a candidate for development would be a in vitro functional assay utilizing a two cell types, such as DC-SIGN$^{(+)}$ cells and effector macrophages (or any or any other cell type which effectively expresses FcγRIIB), where one could measure an increase in FcγRIIB expression in this second cell type. Thus, such a functional in vitro assay would comprise;

(a) providing a first cell type which is a DC-SIGN$^{(+)}$ cell;

(b) providing a second cell type comprising monocyte/macrophages derived from either blood or from an immortalized cell line of this lineage (including but not limited to as THP-1, U937 or HL-60 cells);

(c) co-culturing or resuspending the first and second cell types and incubating these cell types together, both in the presence and absence of a test compound; and, (d) measuring the ability of the test compound to affect expression of the FcγIIRB receptor, wherein an increase in expression of the FcγIIRB receptor indicates a potential agonist to promote an anti-inflammatory response associated with autoantibody mediated inflammation.

Many variations to this theme of a two cell functional assay will be available to the artisan, including but not limited to the use of a control compound (such as a control compound which is an agonist of the DC-SIGN receptor type [e.g., such as a Fc fragment containing a α2,6-linked sialic acid]) in conjunction with the test compound. This type assay may monitor FcRIIB expression by known methods, including cell surface staining, using an antibody (such as 2B6, a high affinity monoclonal antibody that does not cross react with the FcγIIRB receptor [see Rankin et al., 2006, *Blood* 108(7): 2384-2391) or by an FcRIIB-based reporter assay, utilizing components and strategies as described herein. Additionally, the culture of these cell types may be supplemented with additional accessory cells, such as bone marrow derived cells or splenic cells to promote the biological response.

It will also be within the scope of the invention to submit screened compounds which show an in vitro modulation effect on DC-SIGN receptor type to in vivo analysis, preferably by administering the compound of interest to either a transgenic or wild-type animal to measure in vivo effects of the compound on the DC-SIGN receptor type receptor and to further measure biological and physiological effects of compound administration on the non-human animal. These in vivo studies may be done either alone or in combination with a known DC-SIGN receptor type ligand (e.g., α2,6 sialic acid-linked IgG Fc fragment). One or more candidate test compounds may be administered to an animal, and the ability of the candidate test compound(s) to alter one or more characteristics, as compared to a similar animal not treated with the candidate test compound(s), identifies a modulator, such as an agonist of the DC-SIGN receptor type. Thus, such assays can be advantageous as a next step in identifying compounds for development consideration. For example, the various KO models and wild-type mice can be used for in vivo testing of candidate compounds for their effects on several immune disorders, including but not limited transgenic and knock-out models disclosed within the Example section of this specification. A test compound is administered to an animal (e.g., a mouse) and is evaluated based on its ability to reduce a response, such as footpad inflammation associated with injection of K/BxN serum. A known DC-SIGN receptor type ligand (e.g., α2,6 sialic acid-linked IgG Fc fragment) may also be useful in monitoring or comparing the in vivo effect of the test compound. The test compound may be administered by a variety of methods, including, without limitation, intravenously. Thus, in vivo assays involve the use of various animal models, including transgenic animals that have been engineered to have specific defects, or carry markers that can be used to measure the ability of a candidate test compound to reach and effect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for modulators may be conducted using an animal model derived from any of these species.

The methods of detecting the presence or the amount of the complex between a control antibody (e.g., a labeled α2,6 sialic acid-linked IgG Fc fragment) and the DC-SIGN receptor type/lectin domain or the complex between the test compound and the DC-SIGN receptor type/lectin domain are well known in the art. For example, the presence or the amount of the complex may be determined by such methods as, for example, a competition or sandwich ELISA, a radioimmunoassay, a dot blot assay, a fluorescence polarization assay, a scintillation proximity assay, a homogeneous time resolved fluorescence assay, a resonant mirror biosensor analysis, and a surface plasmon resonance analysis.

Thus, in one embodiment, the control antibody, the test compound and/or the DC-SIGN receptor type/lectin domain is directly labeled with a detectable label and may be detected directly. In another embodiment, neither of these molecules is labeled. Instead, a secondary antibody or other molecule that can bind the test compound or the control antibody or the receptor/binding domain is labeled. The amount of the complex can be detected by detecting the presence of the labeled secondary antibody. Other molecules that can bind to antibodies include, without limitation, Protein A and Protein G, both of which are available commercially, for example, from Pierce Chemical Co. (Rockford, Ill.).

Suitable labels are widely known in the art and include various enzymes, prosthetic groups, fluorescent materials, luminescent materials, magnetic agents and radioactive materials. Examples of suitable enzymes include horseradish peroxidase, alkaline phosphatase, p-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; examples of a luminescent material include luminol luciferin, pyrogallol, or isoluminol; an example of a magnetic agent includes gadolinium; and examples of suitable radioactive material include $^{125}I$, $^{131}I$, $^{35}S$ or $^{3}H$.

As noted above, binding of the test compound and/or the control antibody to the DC-SIGN receptor type/lectin domain can be measured by a competition ELISA. In this method, it would be advantageous to use a control antibody with known affinity to the DC-SIGN receptor type/lectin domain as a control substrate (e.g., a labeled α2,6 sialic acid-linked IgG Fc fragment) for reaction with the test compound, which is labeled, and use the test compound as a competitor. The control antibody and/or the test compound may be labeled directly. In another embodiment, the control antibody and the test compound would be unlabeled and a labeled secondary antibody may be added to the reaction in the second step.

In a sandwich ELISA, the DC-SIGN receptor type/lectin domain is immobilized on a solid carrier and is brought into contact with a liquid containing the test compound and/or the control antibody. Then the quantity of the bound test compound is determined by adding a second antibody which is labeled with a detectable label such as a radioactive atom, a fluorescent or luminescent group or, in particular, an enzyme (for example horseradish peroxidase (HRP)). If the test compound is a human IgG, then the second antibody may be an anti-human-IgG antibody. The amount of the bound second antibody is then determined by measuring the activity, for example the enzyme activity of the label. This activity is a measure of binding of the test compound to the DC-SIGN receptor type/lectin domain. Alternatively, the test compound may be immobilized and a mixture containing the receptor/binding domain and/or the control antibody, is added. In this embodiment, the secondary antibody would be used against the receptor/binding domain. It is important that the secondary antibody binds an epitope of its target, which is not affected by binding of the test compound and the lectin domain.

A radioimmunoassay can also be used in determining the extent of binding of the DC-SIGN receptor type/lectin domain to the test compound and/or the control antibody. In the first step of this method, radioactively-labeled test compound is mixed with the lectin domain. The test compound may be labeled by, for example, radioactive isotopes of hydrogen, sulfur, carbon, etc. In the second step, non-labeled test compound is added to the mix in the known quantities and the test compound-receptor/lectin domain complexes are removed from the mixture by, for example, precipitation. The amount of labeled unbound test compound is then determined.

A dot blot procedure can also be used for this analysis. The use of the dot blot procedure eliminates the need to perform electrophoresis and allows rapid analysis of a large number of samples. In one embodiment of this method, different dilutions of the DC-SIGN receptor type/lectin domain can be placed on a membrane, such as, for example, nitrocellulose membrane, and contacted with radioactively or fluorescence labeled test compound.

A person skilled in the art will appreciate that the test compound does not have to be labeled. In that case, after incubating the membrane-bound DC-SIGN receptor type/lectin domain with the test compound, a secondary antibody, which is labeled, is added to the reaction. The amount of signal produced by the label (radioactivity, light, color, etc) can then be quantified.

A fluorescence polarization assay is based on the principle that a fluorescent tracer, when excited by plane polarized light of a characteristic wavelength, will emit light at another characteristic wavelength (i.e., fluorescence) that retains a degree of the polarization relative to the incident stimulating light that is inversely related to the rate of rotation of the tracer in a given medium. As a consequence of this property, a tracer test compound with constrained rotation, such as in a viscous solution phase or when bound to another solution component, such as an antibody with a relatively lower rate of rotation, will retain a relatively greater degree of polarization of emitted light than if in free solution. Thus, a person of skill in the art can label the DC-SIGN receptor type/lectin domain with an appropriate label and contact the labeled this receptor/binding domain with the test compound and/or the control antibody. The fluorescence polarization assays can be conducted in commercially available automated instruments such as IMx®, TDx®, and TDxFLx™. (Abbott Laboratories, Abbott Park, Ill.).

The DC-SIGN receptor type/lectin domain can be coupled to a scintillation-filled bead in a scintillation proximity assay. Binding of radio-labeled test compounds and/or control antibody would result in emitted light which can be quantified on a scintillation counter. Commercial kits for the scintillation proximity assay are currently available and may be purchased from, for example, Amersham Life Science (Piscataway, N.J.).

In a homogeneous specific binding assay, a conjugate is formed between a binding test compound (i.e. the test compound, the DC-SIGN receptor type/lectin domain or the control antibody) and coupled to a label, which is chosen in such a way that it behaves differently depending on whether the binding test compound is bound or free. Thus, in one embodiment of the method, different samples containing known amounts of labeled test compounds and/or control antibody in a liquid medium can be contacted with a solid matrix coated with or impregnated with the DC-SIGN receptor type/lectin domain. In another embodiment, the test compound and/or the control antibody may be placed onto a solid carrier and contacted with different liquid samples containing known amounts of the labeled DC-SIGN receptor type/lectin domain. Examples of labels suitable for this method are chemiluminescent compounds and enzymes, as disclosed above. Change in chemiluminescence can be measured, thus reflecting on the relative amount of bound modified antibody candidates.

Surface plasmon resonance analysis is based on quantifying the intensity of electromagnetic waves, also called surface plasmon waves, which may exist at the boundary between a metal and a dielectric. Such waves can be exited by light which has its electric field polarized parallel to the incident plane (i.e., transverse magnetic (TM) polarized). In this method, one of the reagents (i.e., the DC-SIGN receptor type/lectin domain, the test compound, or, optionally, the control antibody) is coupled to the dextran layer (covering the metal film) of a sensor chip and solutions containing different concentrations of the other reagent (i.e. the test compounds and/or the control antibody, in an embodiment where the DC-SIGN receptor type/lectin domain is coupled to the dextran layer) are allowed to flow across the chip. Binding (association and dissociation) is monitored with mass sensitive detection. BIACORE® (Biacore AB, Uppsala, Sweden) equipment can be used for this method. Other modifications of these assays not disclosed in this application will be apparent to a person of ordinary skill in the art. The claims of the present invention include all such modifications.

For the assays disclosed herein, the artisan will understand that in certain situations the amount of the complex of interest (e.g., the complex between the DC-SIGN receptor type/lectin domain and the test compound) may be measured indirectly. For example, if a total amount of the test compound or the receptor/lectin domain is known, the amount of unbound test compound or the unbound DC-SIGN receptor type/lectin domain may be determined. The amount of the unbound compound is an indirect measure of the amount of the compound within the complex.

The present invention also relates to methods of treating one or more immune disorders, as disclosed herein, through administration of a modulator (such as a DC-SIGN receptor type agonist) which directly affects the DC-SIGN receptor, modulators identified initially through these cell- or membrane-based screens and/or through assays utilizing appropriate transgenic animals disclosed herein. Such a DC-SIGN receptor type agonist may be identified through the methods described herein and will be useful in treating immune disorders, including but not limited to immune thrombocytopenia (ITP), autoimmune hemolytic anemia (AHA), systemic lupus erythematosus (SLE), Kawsaki's disease (an acute vasculitic syndrome), sclerodema, rheumatoid arthritis (RA), Chronic Inflammatory Demyelinating Polyneuropathy (CIPD), phemigus and other autoantibody mediated inflammatory conditions. The present invention relates in part to a compound which acts to modulate a DC-SIGN receptor type (e.g., such as an agonist of the receptor), such that the compound modulates the DC-SIGN receptor type so as to mediate a therapeutically effective signal from a DC-SIGN$^{(+)}$ cell to a second effector macrophage, causing an increase in expression of the FcγRIIB receptor, which in turn inhibits the cellular-mediated inflammatory response normally generated from these macrophages in response to relevant autoantibodies. To this end, the present invention further relates to a pharmaceutical composition which comprises such a compound in combination with at least one pharmaceutically effective excipient, such that this pharmaceutical composition is present in a therapeutically effective concentration.

Any of the compositions described herein may be comprised in a kit. In a non-limiting example, a DC-SIGN receptor type, control antibody and/or additional agent, may be comprised in a kit. The kits will thus comprise, in suitable container means, a DC-SIGN receptor type. The components of the kits may be packaged either in aqueous media or in lyophilized form. The container means of the kits will generally include at least one vial, test tube, flask, bottle, syringe or other container means, into which a component may be placed, and preferably, suitably aliquoted. When there are more than one component in the kit, the kit also will generally contain a second, third or other additional container into which the additional components may be separately placed. However, various combinations of components may be comprised in a vial. The kits of the present invention also will typically include a means for containing a DC-SIGN receptor type, control antibody and/or additional agent, and any other reagent containers in close confinement for commercial sale. Such containers may include injection or blow-molded plastic containers into which the desired vials are retained.

As used herein, the term "DC-SIGN receptor type" may be any mammalian C-type lectin receptor type known to bind intracellular adhesion molecule (ICAM)-3 (CD50), including but not limited to DC-SIGN (a human dendritic cell-specific adhesion receptor [CD209] found on dendritic cells), SIGN-R1 (the murine homologue of DC-SIGN, known to be expressed on splenic marginal zone macrophages), and DC-SIGNR ("DC-SIGN-related," a human homologue of DC-SIGN expressed on sinusoidal endothelial liver cells and endothelial cells in lymph node tissue), as well as any relevant mammalian homologues or isoform thereof, such as well as various homologues, splice variants and/or isoforms, such as disclosed in US 2005/0221291 A1 (Ahuha et al).

As used herein, the term "test compound" or "compound" may refer to any molecule that may potentially enhance the activity of a DC-SIGN receptor type (i.e., act as an agonist of the receptor) or potentially inhibit the activity of a DC-SIGN receptor type (i.e., act as an antagonist of the receptor). Such a test compound may be a protein or fragment thereof, a small molecule such as an organic molecule, or even a nucleic acid molecule. Given the state of the art in treating autoimmune disorders via IVIG administration, it is possible that a most effective test compound identified through the assays disclosed herein will be an antibody that 'interacts' with a DC-SIGN receptor type so as to bind, mediate and stimulate an secondary effector cell, causing an increase in expression of the FcγRIIB receptor. It may be that the antibody in question may be more useful as an Fc fragment, and possibly an Fc fragment containing sialic acid, as described in WO 2007/117505, which is hereby incorporated by reference in its entirety. Using lead compounds to help develop improved compounds is know as "rational drug design" and includes not only comparisons with know agonists or antagonists of the receptor, but predictions relating to the structure of target molecules. On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds. Test compounds may include fragments or parts of naturally-occurring compounds, or may be found as active combinations of known compounds, which are otherwise inactive. Such test compounds may be isolated and identified from natural sources, such as animals, bacteria, fungi, plant sources, including leaves and bark, and marine samples may be assayed as candidates for the presence of potentially useful pharmaceutical agents. It will be understood that the test compounds to be screened as potential pharmaceutical agents could also be derived or synthesized from chemical compositions or man-made compounds. Thus, as noted throughout this specification, it is understood that the candidate test compound identified by the present invention may be an antibody (including but not limited to an Fc fragment or single chain antibody), peptide, polypeptide, polynucleotide, antisense molecule, ribozyme or any other compounds that may be designed through rational drug design starting from known inhibitors or stimulators.

As used herein, the term "Fc fragment" or "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof.

As used herein, the term "binding domain" refers to the region of a polypeptide that binds to another molecule. In the case of an FcR, the binding domain can comprise a portion of a polypeptide chain thereof (e.g., the at chain thereof) which is responsible for binding an Fc region. One exemplary binding domain is the extracellular domain of an FcR chain.

As used herein, the term "lectin domain" or "LBD" may refer to a portion of a lectin domain, also referred to as the C-type lectin domain (see Geijtenbeek, et al., 2000, Cell 100:575-585) or carbohydrate-recognition domain [CRD; see Wu and KewalRamani, 2006, Nat. Rev. Immun. 6(11): 859-868] (e.g., from about amino acid 241-404 of human DC-SIGN) of a DC-SIGN receptor type. An LBD useful herein will be an LBD which may be have affinity for a known modulator or test compound.

As used herein, "control antibody" refers to an antibody, or an Fc fragment, etc. which has a measurable affinity to a lectin domain of a DC-SIGN receptor type so as to be useful to use as a baseline value of binding to the receptor. An example, but not provided as a limitation, of a control antibody is an antibody or fragment (such as an Fc fragment) which contains comprises an α2,6 sialic acid linkage 2,6 Fc. Such a control antibody may (but is not required to possess) have the ability to promote an in vivo anti-inflammatory response as described herein.

As used herein, "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

As used herein, "antibody fragments", may comprise a portion of an intact antibody, generally including the antigen binding or variable region of the intact antibody or the Fc region of an antibody which retains FcR binding capability. Examples of antibody fragments include linear antibodies; single-chain antibody molecules; and multispecific antibodies formed from antibody fragments. The antibody fragments preferably retain at least part of the hinge and optionally the CH1 region of an IgG heavy chain. More preferably, the antibody fragments retain the entire constant region of an IgG heavy chain, and include an IgG light chain.

It should be appreciated by those of skill in the art that the techniques disclosed herein represent techniques that will function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. To describe the instant invention in more details, several non-limiting illustrative examples are given below.

EXAMPLES

Materials and Methods—The following materials and methods apply to all examples, unless specifically noted otherwise.

Mice—C57BL/6, NOD, JHD[7], $CD4^{-/-}$, and $Rag1^{-/-}$ mice were purchased from the Jackson Laboratory (Bar Harbor, Me.). KRN TCR C57BL/6 mice were gifts from D. Mathis and C. Benoist (Harvard Medical School, Boston, Mass.) were bred to NOD mice to generate K/BxN mice. $SIGN\text{-}R1^{-/-}$ mice were provided by A. McKenzie and C. G. Park, and M. Carroll and M. Botto provided $Clq^{-/-}$ mice. Age-matched female mice at 5-8 weeks of age were used for all experiments and maintained at the Rockefeller University animal facility. All experiments were done in compliance with federal laws and institutional guidelines and have been approved by the Rockefeller University (New York, N.Y.). K/BxN serum is prepared as described previously (Bruhns et al., *Immunity* 18, 573 (April 2003)). IVIG or α2,6 (1 g/kg or 0.033 g/kg, respectively) was injected 1 hr before K/BxN serum injection. Inflammation for each paw was scored 0-3 (0, no swelling; 3 entirely swollen) and added for total clinical score. For surgical procedures, mice were anestitized and spleens cauterized under sterile conditions, wounds stapled, and mice allowed to recover for one week. Mice receiving blocking antibody treatment received 100 μg of antibody 1 hour (for α-SIGN-R1 and α-MARCO) or 24 hours (for TKO-SIGN-R1) prior to IVIG.

IVIG Fc preparations—Fc fragments from IVIG were generated as previously described (Kaneko, Nimmerjahn, and Ravetch, *Science* 313, 670 (Aug. 4, 2006); Samuelsson, Towers, and Ravetch, *Science* 291, 484 (Jan. 19, 2001)). Preparations were confirmed by lectin blotting using SNA-biotin (Vector) for α2,6 sialic acid linkages and for α2,3 sialic acid linkages. Fc preparations were treated with neuraminidase (New England Biolabs) or PNGaseF (New England Biolabs) to remove sialic acid or N-linked glycans per according to manufacturer's instructions. Some neuraminidase-treated Fcs were sialylated in vitro with α2,3 sialyltransferase to generate α2,3 Fcs. Proteins were labeled with Alexa-647 according to manufacturer's instructions (Invitrogen).

FACS sorting—Mouse spleens were removed, digested with Liberase blendzyme 3 (Roche), and single cell suspensions made. Next, red blood cells were lysed, and FcRs blocked with 2.4G2 (BD Biosciences). Cells were then stained with α-MARCO-PE (AbD Serotec), α-CD169-FITC (AbD Serotec), and α-F4/80-biotin (AbD Serotec) followed by PerCP-streptavidin (BD Biosciences), and sorted using a FACS Aria (BD Biosciences). The sorted populations were then pulsed with 1 μg of Alexa647 label Fcs and reanalyzed using a FACSCalibur (BD Biosciences).

α2,6 Fc Binding—$1\times10^5$ cells per well were plated in 24-well plates and incubated overnight. The next day, the cells were treated with 2.4G2, and then pulsed with 1 μg/well of Alexa-647 label protein for 1 hour at 37° C. Cells were mechanically removed and analyzed by flow cytometry. For immunohistochemistry, the same numbers of cells were plated onto circular coverslips placed in 24-well plates, these cells were similarly pulsed, stained with DAPI, and the coverslips transferred to slides and analyzed using an Axiovert fluorescent microscope (Zeiss). Fluorescent intensities and exposure times were normalized for all samples.

Histology—Spleens were removed, frozen in OCT freezing media (Sakura Finetek, Japan), and 4 μm sections were cut, fixed in cold acetone, stained with α-SIGN-R1-Alexa647 (eBioscience), α-MARCO (Serotec), α-CD169 (Serotec), α-CD11c-FITC, F4/80-PE, and imaged on a Zeiss Axiovert fluorescent microscope. Ankle joint histology was preformed as previously described (Bruhns et al., *Immunity* 18, 573 (April 2003)), and imaged at 100× using an Axiovert light microscope (Zeiss).

Kinetics of IVIG accumulation in the spleen—Mice were administered IVIG and sacrificed 0 minutes, 10 minutes, 60 minutes, and 1 day later. Spleens sections were examined for IVIG localization (α-human IgG Fc) along with $CD169^+$ metallophillic marginal zone macrophages, $MARCO^+$ marginal zone macrophages, or $CD11c^+$ dendritic cells and red pulp $F4/80^+$ macrophages. 200× fluorescent images were normalized for exposure times and intensities.

Figure 4A:
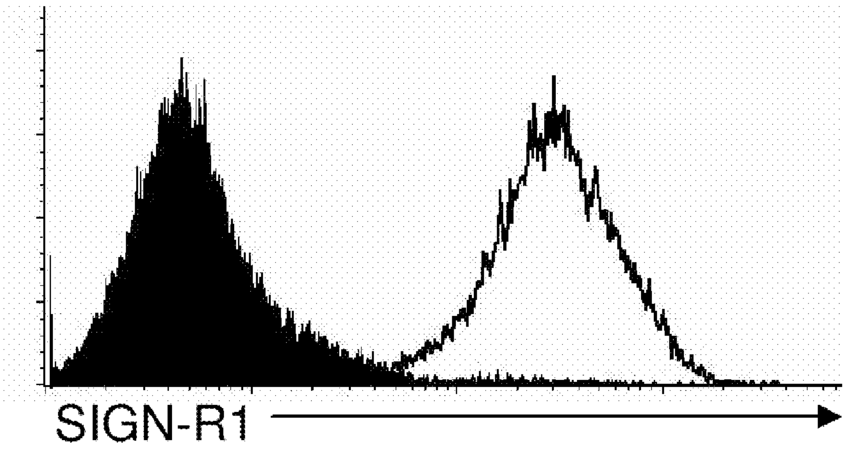
FIG. 4A-D show α2,6 Fc binding to Siglecs. (A) SIGN-R1 transfected cells were confirmed by assessing SIGN-R1 expression on Raw-247 cells (black histogram) and stably transfected Raw-247 cells (Raw-SIGN-R1, white histogram) by flow cytometry. (B) Raw-247 and SIGN-R1 expressing Raw-247 cells were pulsed with fluorochrome-labeled α2,6 Fcs, with or without C1q added to the media, and binding analyzed by FACS. MFI ratios of Raw-SIGN-R1 to Raw cells are plotted, representative of 3 experiments. Flat well plates were coated with Siglec-Fc chimeras of mouse sialoadhesion (Siglec-1) extracellular domains (mSND)-3), a binding-deficient sialoadhesion (mSND)-3R97A4), human CD22 (hCD22), human CD33 (hCD33), mouse MAG (mMAG), human Siglecs 5-10 (hSiglec-5-10), and fetuin. The chimeras were then probed with (C) α2,6 Fc or (D) SA tx Fc immune complexes, developed, and analyzed.
Figure 4B:
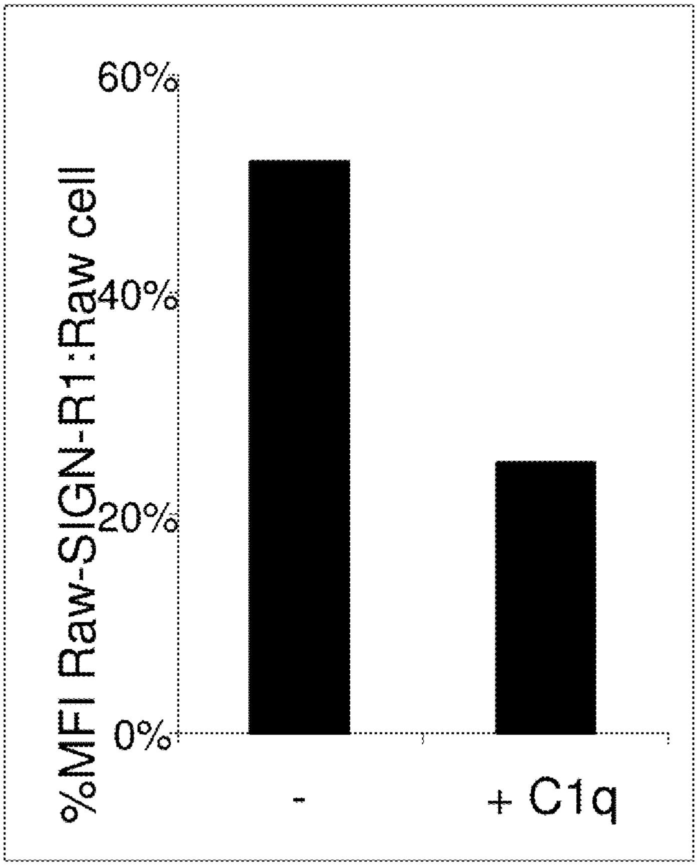

Confirmation of SIGN-R1 expressing cell lines and α2,6 Fc binding to Siglecs—SIGN-R1 transfected cells were confirmed by assessing SIGN-R1 expression on Raw-247 cells and stably transfected Raw-247 cells by flow cytometry (FIG. 4A). Next, Raw-247 cells or SIGN-R1 expressing cells were pulsed with FITC-dextran, stained with DAPI and imaged. Exposure times and intensities were normalized for the 400× images.

Raw-247 and SIGN-R1 expressing Raw-247 cells were pulsed with fluorochrome-labeled α2,6 Fcs, with or without C1q added to the media, and binding analyzed by FACS. MFI ratios of Raw-SIGN-R1 to Raw cells are plotted, representative of 3 experiments. Flat well plates were coated with Siglec-Fc chimeras of mouse sialoadhesion (Siglec-1) extracellular domains (mSND)-3), a binding-deficient sialoadhesion (mSND)-3R97A4), human CD22 (hCD22), human CD33 (hCD33), mouse MAG (mMAG), human Siglecs 5-10 (hSiglec-5-10), and fetuin. The chimeras were then probed with α2,6 Fc or SA tx Fc immune complexes, developed, and analyzed.

Example 1

Macrophages are Required for Anti-Inflammatory Effect of IVIG

To examine the properties of the regulatory macrophage population required for IVIG-mediated immune suppression, a panel of defined mouse strains with defects in specific immune cell populations were treated with arthritis inducing sera (K/BxN) in conjunction with IVIG (FIG. 1). Consistent with previous results, wild type C57Bl/6 mice were protected from inflammation by IVIG, as were mice deficient in B cells ($JHD^{-/-}$) and $CD4^+$ T cells ($CD4^{-/-}$). However, IVIG was not effective in $Rag1^{-/-}$ mice deficient in both B and T cells, nor in spleenectomized mice or as defined previously in the genetic strain op/op (Bruhns, et al., 2003 Immunity 8:573).

Example 2

A Splenic Non-B, Non-T Population and Marginal Zone Architecture are Required for IVIG Immune Suppression The splenic architecture of these mouse strains was examined using an array of marginal zone macrophage markers, including macrophage receptor with collagenous domain (MARCO) (Elomaa et al., *Cell* 80, 603 (Feb. 24, 1995)), sialic acid binding Ig-like lectin-1 (Siglec-1, CD169) (Crocker et al., *Embo J* 10, 1661 (July, 1991); Crocker, J. C. Paulson, A. Varki, *Nat Rev Immunol* 7, 255 (April 2007)), and SIGN-R1 (CD209b) (Kang et al., *Int Immunol* 15, 177 (February, 2003); Geijtenbeek et al., *Blood* 100, 2908 (Oct. 15, 2002)).

Figure 2:
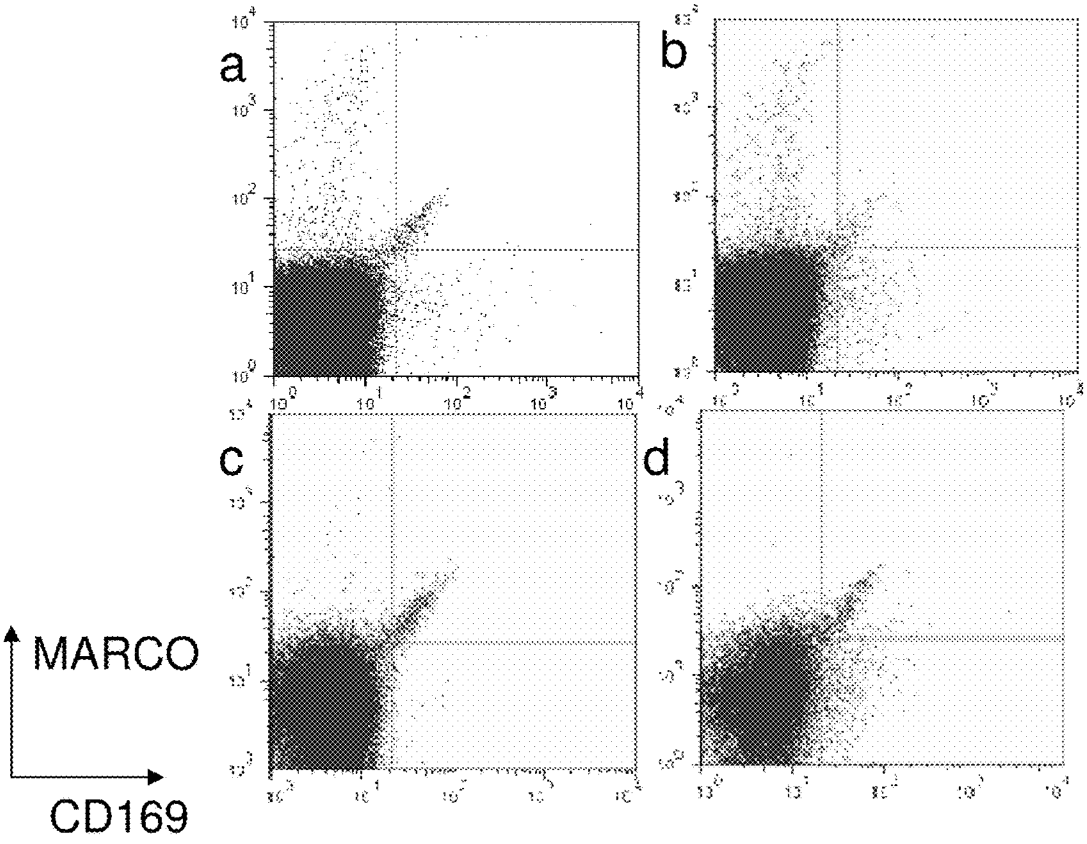
FIG. 2A-D show an analysis of splenic marginal zone macrophages in wild type (A), $CD4^+$ T cell deficient mice ($CD4^{-/-}$, B), B cell deficient mice ($JHD^{-/-}$, C), and mice deficient in both B and T cells ($Rag1^{-/-}$, D) by flow cytometry for $MARCO^+$ (y axis) and $CD169^+$ (x axis) cells.

The marginal zones of wild type Bl/6 mice exhibited a characteristic inner ring of $CD169^+$ marginal zone metallophillic macrophages, encircled by $MARCO^+$ marginal zone macrophages, some of which also expressed SIGN-R1, and had detectable $MARCO^+$ and $CD169^+$ cells by flow cytometry (FIG. 2A). While the defined architecture was disrupted in both B cell and $CD4^+$ T cell deficient mice, all of these macrophage populations were nonetheless present (FIGS. 2B and 2C). In contrast, $Rag1^{-/-}$ mice (FIG. 2D) displayed severely disrupted marginal zone structures, with markedly reduced numbers of $CD169^+$ cells and $MARCO^+$ cells, and no detectable SIGN-R1 staining. Taken together, these results indicate a splenic non-B, non-T population and marginal zone architecture were required for IVIG immune suppression.

Example 3

Anti-Inflammatory Effect of IVIG is Mediated by $MARCO^+$ Marginal Zone Macrophages To determine which splenic macrophage populations interacted with the biologically active component of IVIG, α2,6 Fc, $F4/80^+$ red pulp macrophages, $CD169^+$ metallophillic macrophages, and $MARCO^+$ marginal zone macrophages were sorted from the spleens of C57Bl/6 wild type mice. The cell populations were then pulsed in vitro with fluorescently labeled IVIG Fc preparations with glycans terminating in α2,6 sialic acid (α2,6 Fc), Fc's devoid of sialic acid (sialidase (SA) tx Fc), or with enzymatically deglycosylated Fc's (PNGaseF tx Fc), and reanalyzed by flow cytometry. $F4/80^+$ red pulp macrophages did not bind any of the Fc preparations, while $MARCO^+$ macrophages preferentially bound α-2,6 Fc's when compared to $CD169^+$ macrophages. These results were consistent with in vivo examination of intravenously injected IVIG which demonstrated that IVIG localized with $MARCO^+$ marginal zone macrophages. In these experiments, mice were administered IVIG and sacrificed 0 minutes, 10 minutes, 60 minutes, and 1 day later. Spleens sections were examined for IVIG localization along with $CD169^+$ metallophillic marginal zone macrophages, $MARCO^+$ marginal zone macrophages, or $CD11c^+$ dendritic cells and red pulp $F4/80^+$ macrophages. 200× fluorescent images were normalized for exposure times and intensities.

Example 4

Anti-Inflammatory Effect of IVIG is Mediated by SIGN-R1

Figure 3A:
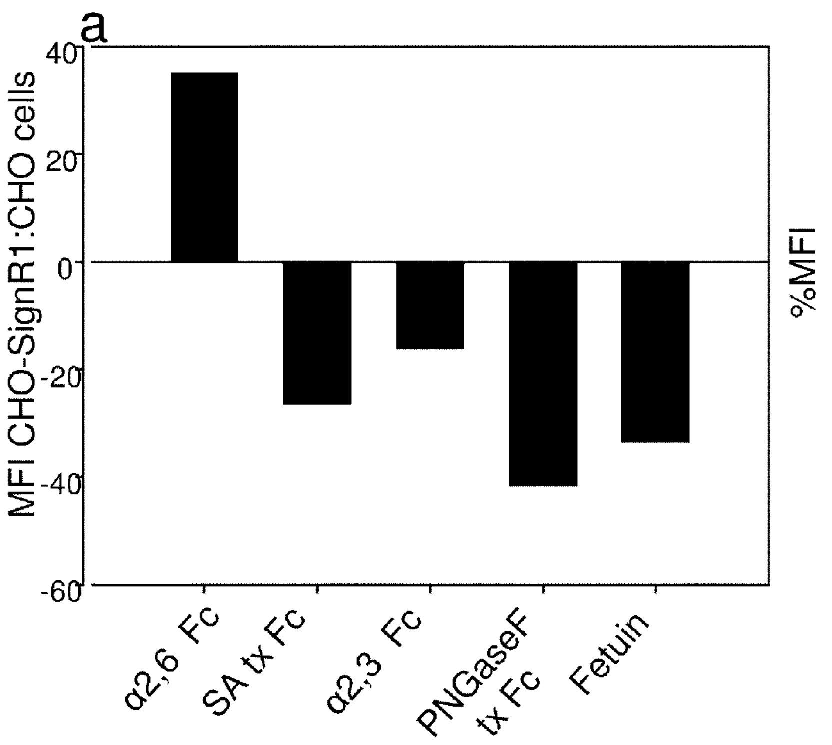
FIG. 3A-C show that SIGN-R1 expressing cells preferentially bind α2,6 Fc fragments. (A) CHO and CHO-SIGN-R1 cells were pulsed with various labeled Fc and fetuin preparations, and analyzed by flow cytometry. Mean fluorescent intensity (MFI) ratios of CHO-SIGN-R1 to CHO cells representative of 4 separate experiments are plotted. (B) In parallel, α2,6 Fc binding to Raw-SIGN-R1 cells was blocked with SIGN-R1-specific antibodies (ERTR-9), but not the isotype control (Rat IgM), and treatment with EDTA abrogated all binding. (C) Cell lines expressing the lectins SIGN-R1, SIGN-R3, mDC-SIGN, hDC-SIGN, and hDEC-205 were pulsed with fluorochrome labeled Fc preparations and analyzed by FACS.
Figure 3B:
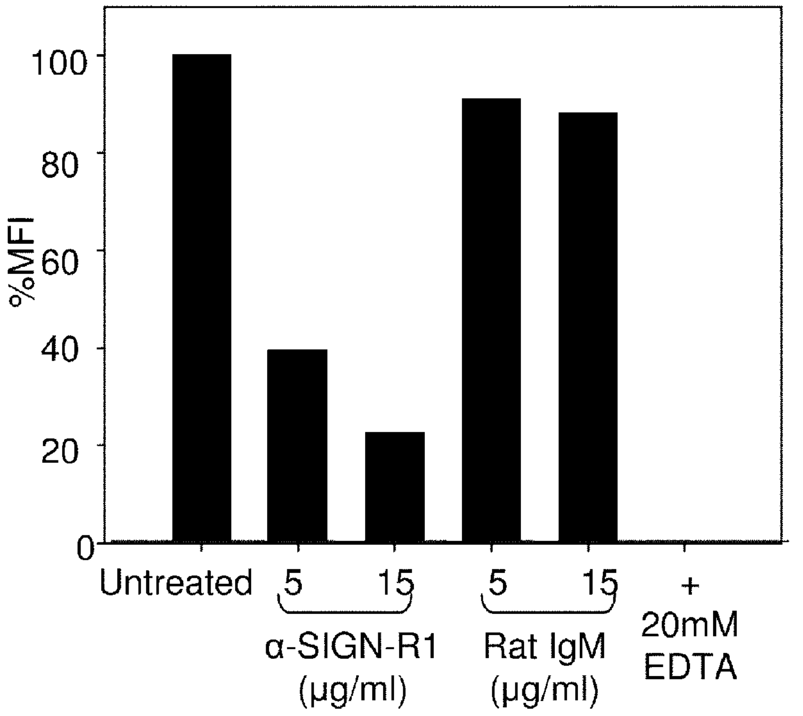
Figure 3C:
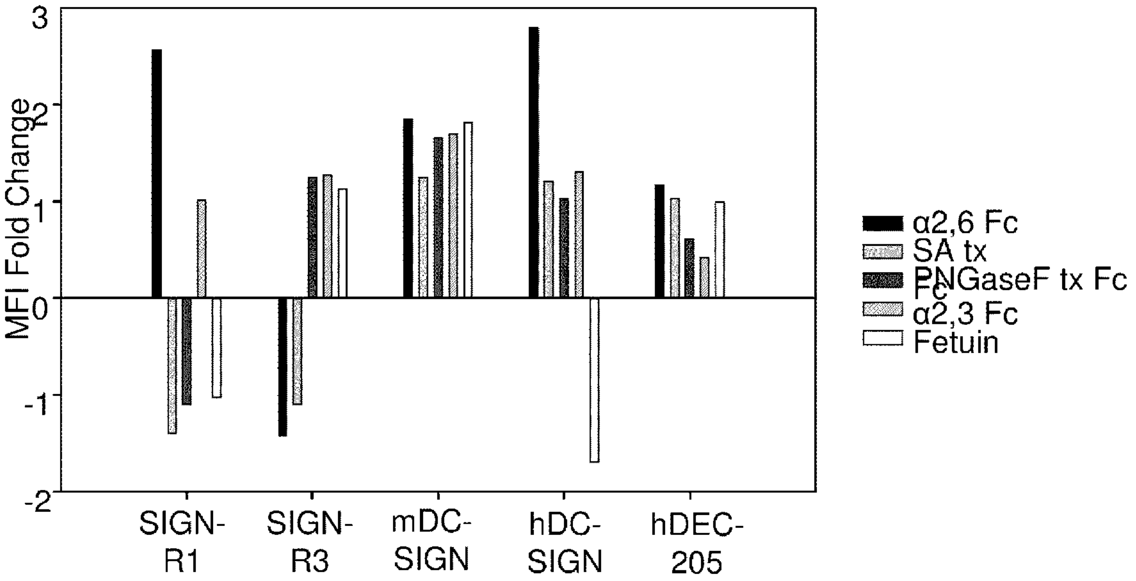
Figures 4C, 4D:
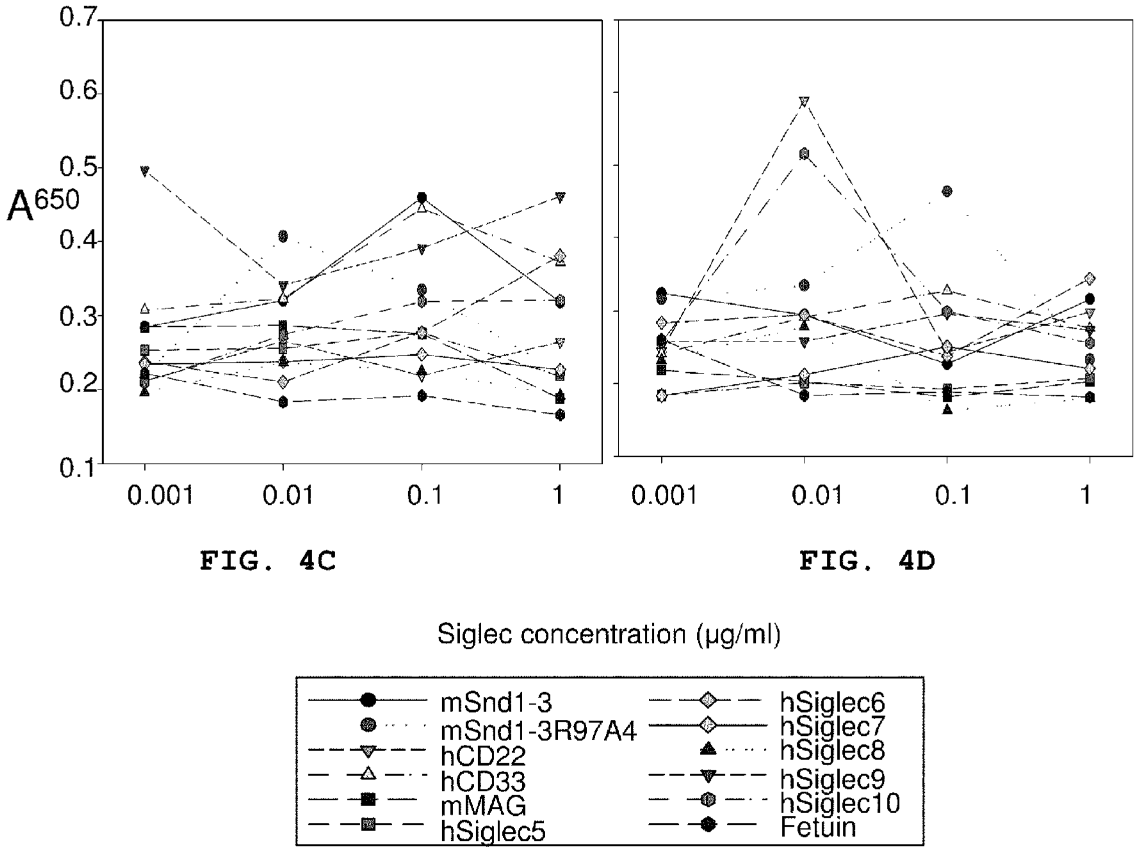

Since $MARCO^+$ marginal zone macrophages were preferentially targeted by IVIG, experiments were performed to determine if a specific receptor expressed on these cells was responsible for binding the α2,6 sialylated Fc. These macrophages express a number of pattern recognition receptors, including the scavenger receptor MARCO (Elomaa et al., *Cell* 80, 603 (Feb. 24, 1995)), and SIGN-R1, a C-type lectin involved in binding of circulating *Streptococcus pneumonia* and dextran (Kang et al., *Proc Natl Acad Sci USA* 101, 215 (Jan. 6, 2004); Lanoue et al., *J Exp Med* 200, 1383 (Dec. 6, 2004)). Therefore, binding studies were performed on macrophage (RAW-247) and CHO cell lines transfected with SIGN-R1 or control lectins such as SIGN-R3 and mDC-SIGN (see FIG. 3A-C and FIG. 4A-D). Only SIGN-R1 expressing cells demonstrated markedly enhanced binding α2,6 Fc's. In contrast, Fc's with glycans terminating in α2,3 sialic acid linkages (α2,3 Fc), asialylated Fc's (SA tx Fc), aglycosylated Fc's (PNGaseF tx Fc), or fetuin, a serum protein with a bi-antennary, complex sialylated glycan similar to that found on IgG Fc (FIG. 3A) did not exhibit specific binding. Additionally, binding of α2,6 Fc's was blocked with an antibody recognizing the lectin binding site of SIGN-R1 (Kang et al., *Int Immunol* 15, 177 (February, 2003)) (FIG. 3B), as did addition of the calcium chelating agent EDTA, indicating the binding was lectin-mediated. The specificity of this binding reaction was further confirmed by demonstrating the absence of binding of α2,6 Fc's to other lectins, including SIGN-R3, human DEC-205 (hDEC-205) and mouse and human Siglecs (FIG. 3C and FIG. 4C,D). The human homoglue of SIGN-R1, DC-SIGN, displayed a binding profile similar to SIGN-R1 (FIG. 3C). mDC-SIGN, in contrast, did not demonstrate specificity for α2,6 Fc.

Example 5

Classical Complement Pathway is Not Involved in Anti-Inflammatory Effect of IVIG Previous studies reported that C1q, the initiator of the classical complement pathway, was capable of binding SIGN-R1 (Kang et al., *Cell* 125, 47 (Apr. 7, 2006)). Because this molecule also interacts with IgG Fc portions, possible involvement of C1q in the interaction of α2,6 Fc's and SIGN-R1 was investigated. Addition of C1q to the binding reaction of sialylated α2,6 Fc's to SIGN-R1 expressing RAW-247 cells resulted in reduced α2,6 Fc binding to SIGN-R1 (FIG. 4B), indicating that C1q was not required for α2,6 Fc binding to SIGN-R1 and likely interfered with the binding interaction. Thus, SIGN-R1 bound the active component of IVIG in a manner dependent on the Fc fragment, the specific carbohydrate linkage necessary for its anti-inflammatory activity, as well as calcium ions required for C-type lectin binding.

Example 6

SIGN-R1 Mediates Anti-Inflammatory Activity of IVIG In Vivo

Figure 5:
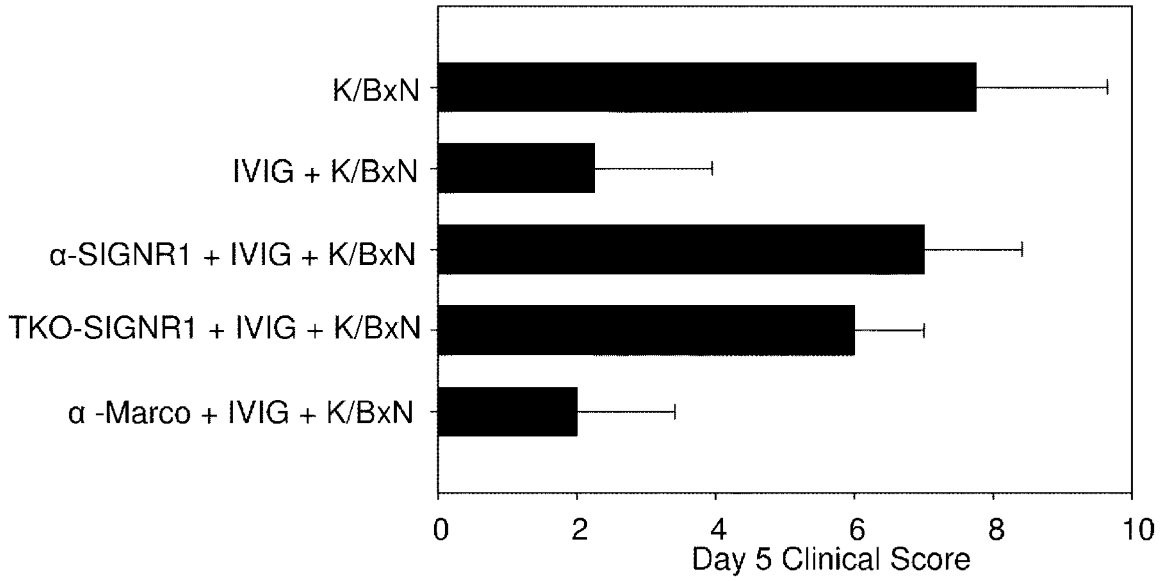
FIG. 5 shows the results of experiments demonstrating that SIGN-R1 blockade abrogates IVIG protection of induced arthritis. C57BI/6 mice were treated with IVIG and K/BxN, some of which were administered blocking antibodies to SIGN-R1 (α-SIGNR1) or Marco (α-Marco), or were induced to down-regulate SIGN-R1 surface expression (TKO-SIGN-R1), and footpad swelling monitored over the next several days. Mean and standard deviation of day 5 clinical scores of 5 mice per group are plotted; * denotes $p<0.001$ as determined by Tukey's post hoc test.
Figure 6:
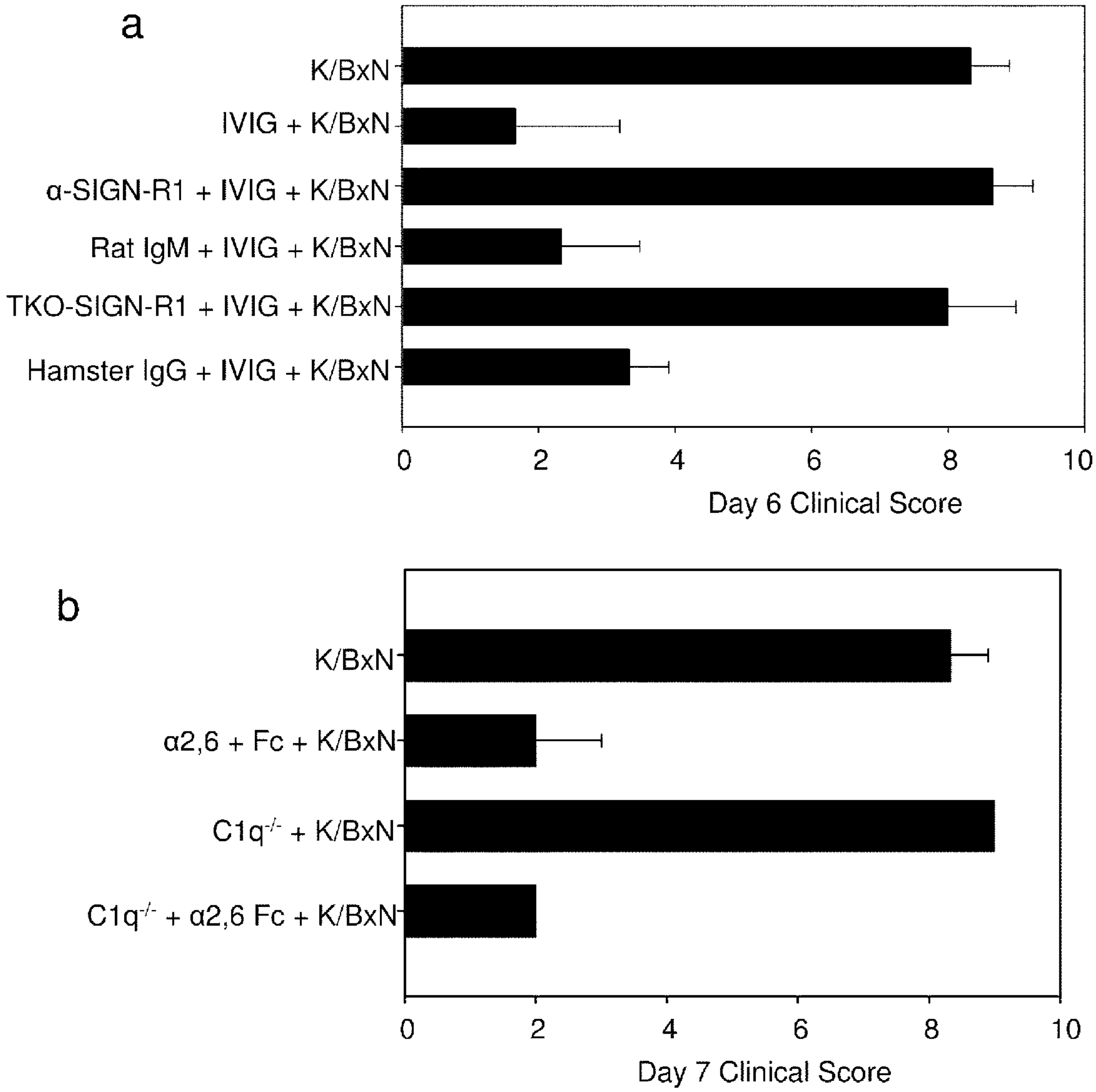
FIG. 6A-B show that C1q was not involved in α2,6 Fc binding to SIGN-R1 or required its anti-inflammatory activity. Mice were treated with K/BxN sera and IVIG, some of which received SIGN-R1 blocking antibodies ERTR-9 (α-SIGN-R1), or SIGN-R1 down-regulating antibodies 22D1 (TKO-SIGN-R1), or appropriate isotype controls (Rat IgM and Hamster IgG, respectively). Footpad swelling was monitored over the next seven days. Day 6 clinical scores of 5 mice per group are plotted in terms of mean and standard deviation. B. Wild type and C1q/C57Bl/6 mice were injected with K/BxN sera, some of which received (α2,6 Fcs, and footpad swelling was monitored over the next several days in terms of clinical scores.

Next, the in vivo requirement for SIGN-R1 binding by IVIG to mediate its anti-inflammatory activity was examined. Joint inflammation was induced in wild type C57Bl/6 mice with K/BxN serum and the ability of IVIG to attenuate tissue pathology was examined in the presence of antibodies that disrupted either SIGN-R1 expression (TKO-SIGN-R1) or its lectin domain (α-SIGN-R1) (Kang et al., *Proc Natl Acad Sci USA* 101, 215 (Jan. 6, 2004)). Mice were treated with K/BxN sera and IVIG, some of which received SIGN-R1 blocking antibodies ERTR-9 (α-SIGN-R1), or SIGN-R1 down-regulating antibodies 22D1 (TKO-SIGN-R1), or appropriate isotype controls (Rat IgM and Hamster IgG, respectively). Footpad swelling was monitored over the next seven days. Day 6 clinical scores of 5 mice per group are plotted in terms of mean and standard deviation. Both antibodies abrogated the anti-inflammatory activity of IVIG (FIG. 5). In contrast, neither α-MARCO antibodies (van der Laan et al., *J Immunol* 162, 939 (Jan. 15, 1999)) nor isotype controls of SIGN-R1 antibodies had effect on IVIG activity (FIG. 5 and FIG. 6A). These results are consistent with the inventors' previous observation that op/op mice were unable to mediate the anti-inflammatory activity of IVIG (Bruhns et al., *Immunity* 18, 573 (April 2003)), as op/op mice have no SIGN-R1 expression detectable by fluorescent immunohistochemistry. Similarly, SIGN-R1 expression was undetectable in TKO-SIGN-R1 treated, indicating this treatment effectively downregulated SIGN-R1 expression but did not effect marginal zone structure, while α-SIGN-R1 isotype control antibodies did not effect SIGN-R1 expression. Thus, the correlation of SIGN-R1 expression in mice protected by IVIG, binding of α2,6 Fcs to SIGN-R1, and the ability to modulate IVIG protection in models of inflammation in vivo by blockage of this receptor strongly supported a role for this C-type lectin in the anti-inflammatory activity of IVIG.

Example 7

IVIG Anti-Inflammatory Activity is Abrogated in SIGN-R1$^{-/-}$ Mice

Figure 7:
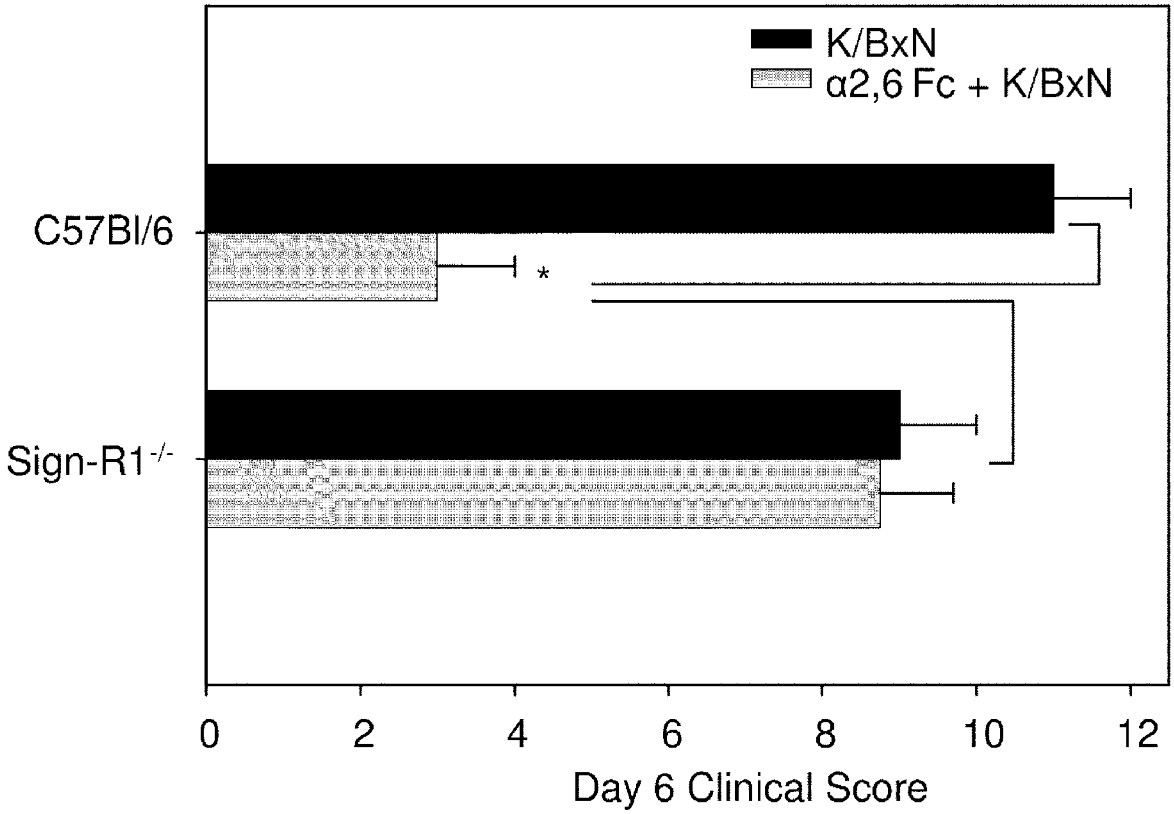
FIG. 7 shows that α2,6 Fc's do not suppress induced arthritis in $SIGN\text{-}R1^{-/-}$ mice. C57Bl/6 and $SIGN\text{-}R1^{-/-}$ mice were administered K/BxN sera (black bars), some of which received α2,6 Fc 1 hour earlier (α2,6 Fc+K/BxN, gray bars). Footpad swelling was monitored over the next several days in terms of clinical scores. Means and standard deviations of 3-4 mice per group are plotted. *$p<0.05$ as determined by ANOVA followed by Tukey's post hoc.

Definitive confirmation of the necessity of SIGN-R1 expression for the anti-inflammatory activity of IVIG was demonstrated by the lack of IVIG protection in SIGN-R1 knock-out mice (SIGN-R1$^{-/-}$, FIG. 7) (Lanoue et al., *J Exp Med* 200, 1383 (Dec. 6, 2004)). While α2,6 Fcs inhibited K/BxN induced arthritis in wild type C57Bl/6 mice, their protective capacity was abrogated in SIGN-R1 deficient mice (SIGN-R1$^{-/-}$). In contrast, C1q$^{-/-}$ displayed K/BxN induced joint inflammation that was protected by α2,6 Fc (FIG. 6B), consistent with the data indicating C1q was not involved in α2,6 Fc binding to SIGN-R1 or required its anti-inflammatory activity. These in vivo data are summarized in Table 1.

TABLE 1

IVIG protection and SIGN-R1 expression in various mouse strains.

| Mouse Strain/ Treatment | Phenotype | K/BxN arthritis | IVIG protection | Marginal zone/ SIGN-R1 expression |
|---|---|---|---|---|
| C57Bl/6 | Wild type | +++ | Yes | Intact/Yes |
| JHD$^{-/-}$ | No B cells | ++ | Yes | Disrupted/Yes |
| CD4$^{-/-}$ | No CD4+ T cells | ++ | Yes | Disrupted/Yes |
| Rag1$^{-/-}$ | No T nor B cells | ++++ | No | Disrupted/No |
| IL-10$^{-/-}$ | Cannot make IL-10 | ++ | Yes | |
| op/op | No CSF-1 dependent Mϕ | ++ | No | Intact/No CD169, No SIGN-R1 |
| FcγRIIb$^{-/-}$ | No inhibitory FcγIIb | +++ | No | Intact/Yes |
| Splenectomy | No spleen | ++++ | No | N.A. |
| α-SIGN-R1 (ER-TR9) | Blockage of SignR1 binding site | ++++ | No | Intact/Yes |
| TKO-SIGN-R1 (22D1) | Transient loss of SignR1 expression | ++++ | No | Intact/No |
| α-Marco (ED31) | Blockage of Marco | +++ | Yes | Intact/Yes |
| C1q$^{-/-}$ | Initiator of classical complement pathway | +++ | Yes | Intact/Yes |
| SIGN-R1$^{-/-}$ | Sign-R1 deficient, no dextran binding | ++++ | No | Intact/No |

The results presented in this Example section here establish SIGN-R1 as a receptor necessary for the anti-inflammatory activity of IVIG and α2,6 Fc and identify a novel pathway by which sialylated IgG promotes an anti-inflammatory state. The pathway is conserved in both mice and humans by virtue of the specificity of the lectin binding to α2,6 Fc, albeit through different target cells. The human homologue of SIGN-R1, DC-SIGN, is expressed on dendritic cells and is thus more broadly distributed than mSIGN-R1, whose expression on splenic marginal zone macrophages is required for the activity of IVIG. This difference in anatomical requirement is consistent with the clinical observation that IVIG is potent as an anti-inflammatory in splenectomized patients, in contrast to the situation in mice. The fact that SIGN-R1 and hDC-SIGN (Kang et al., *Int Immunol* 15, 177 (February, 2003); Galustian et al., *Int Immunol* 16, 853 (June, 2004)) have been shown to interact with viral and bacterial (Tailleux et al., *J Exp Med* 197, 121 (Jan. 6, 2003); Pohlmann et al., *J Virol* 77, 4070 (April 2003); Geijtenbeek et al., *Cell* 100, 587 (Mar. 3, 2000)) pathogens also suggests a mechanism by which displacement of sialylated Fc by these organisms may shift the response away from the steady state to an active, inflammatory one. Subversion of this pathway by some pathogens may inappropriately maintain an anti-inflammatory state and thus prevent effective immunity from becoming established.

Example 8

SIGN-R1 Binds 2,6 Sialylated Fc

Figure 8:
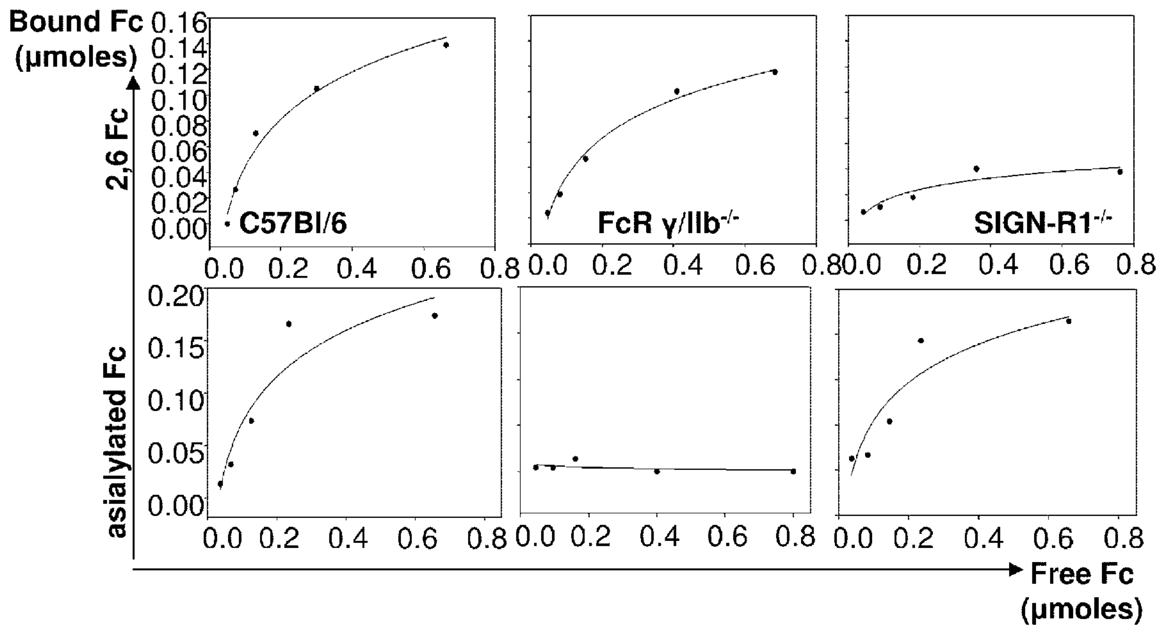
FIG. 8 shows resident peritoneal macrophages isolated from C57BL/6 (left column) $FcR\gamma/IIb^{-/-}$ (middle column), $SIGN\text{-}R1^{-/-}$ (right column) mice were pulsed with increasing concentrations of 2,6-sialylated Fcs (top row) or asialylated Fcs (bottom row). The amount of bound Fcs were determined and are plotted versus the free, unbound Fcs, and are representative of two separate experiments.

To determine whether SIGN-R1 had the ability to bind to this sialylated glycoprotein ligand. A transfected macrophage cell line that expressed SIGN-R1 (RAW-SIGN-R1) selectively bound sialylated Fcs compared with untransfected cells (FIG. 8). To demonstrate that 2,6 sialylated Fcs and asialylated Fcs bound to specific, nonoverlapping receptors on macrophages, we harvested resident peritoneal, SIGN-R1$^{+}$ macrophages derived from wild type C57BL/6 mice, from mice lacking all IgG Fc receptors (Takai et al., 1994 *Cell* 76:519-529; Takai et al., 1996 *Nature* 379:346-349) (FcRγ/IIb$^{-/-}$) or from SIGN-R1 deficient mice (Lanoue A et al., 2004 *J Exp Med* 200:1383-1393) (SIGN-R1$^{-/-}$) for quantitative binding assays. Fcγ receptor-deficient macrophages (FcRγ/RIIb$^{-/-}$) bound α2,6-Fcs, while SIGN-R1$^{-/-}$ macrophages preferentially bound asialylated Fcs (FIG. 8). These results are consistent with our previous results that canonical IgG Fc receptors bind to sialylated Fc with a 10-fold lower affinity than asialylated Fc (Nimmerjahn et al., 2007 *J Exp Med* 204:11-15, Kaneko et al., 2006 *Science* 313:670-673, Anthony et al., 2008 Science 320:373-376). Thus, the 2,6-sialylation of the IgG Fc glycan converts the molecule from one able to productively engage FcγR5 and mediate an inflammatory response, to a species that has reduced FcγR binding but acquires the ability to engage a macrophage expressed lectin, SIGN-R1, and mediate an anti-inflammatory response.

Example 9

DC-SIGN Binds 2,6 Sialylated Fc

Figure 9:
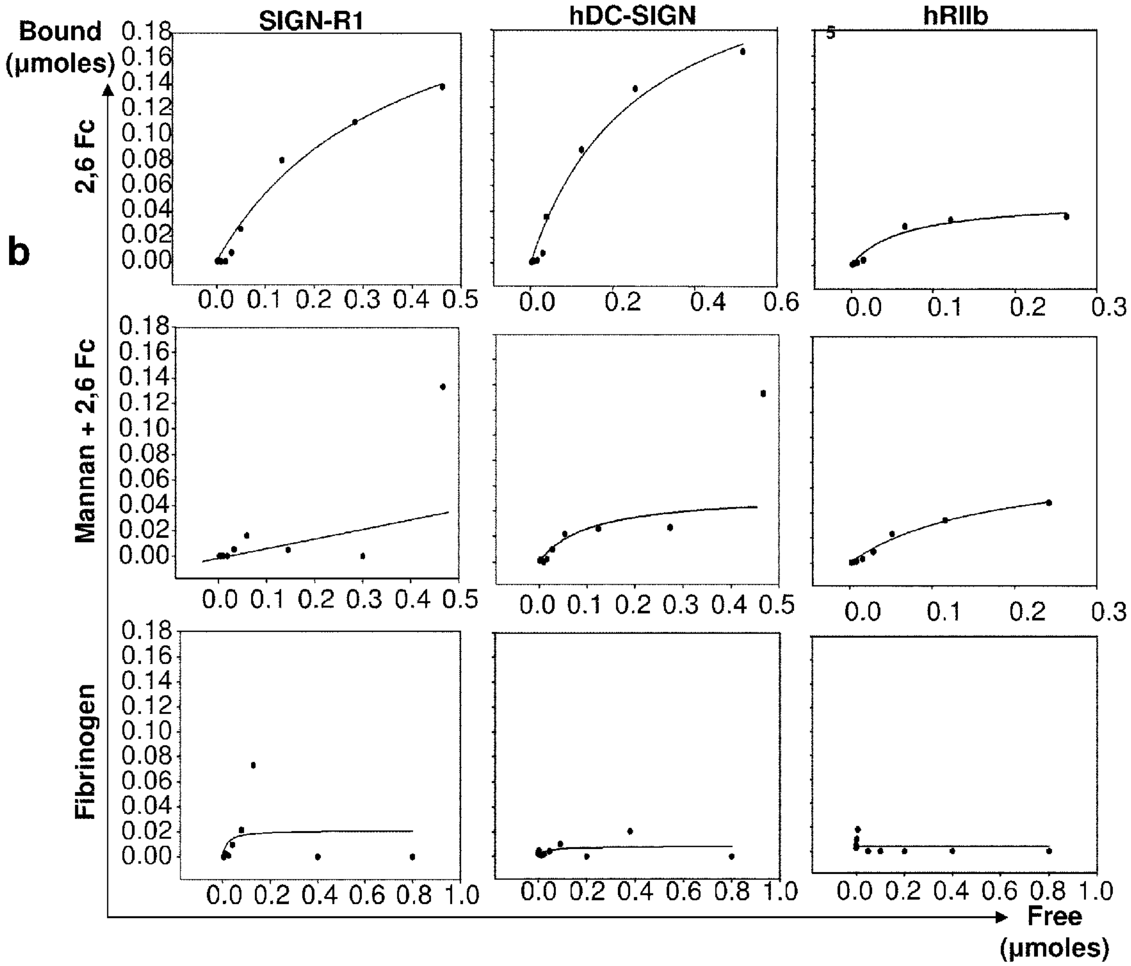
FIG. 9 shows CHO cells expressing SIGN-R1 (left column), hDC-SIGN (middle column), or hFcRγIIb (right column) were pulsed with 2,6-Fcs (top row), incubated with manna before 2,6-Fc pulse (middle row), or pulsed with fibrinogen (bottom row). The amount of bound glycoproteins was determined, and is plotted verses the free, unbound protein.

The binding specificity of DC-SIGN in transfected CHO cells compared with SIGN-R1 expressing CHO cells was examined. Both DC-SIGN and SIGN-R1 expressing CHO cells bound 2,6-sialylated Fc (FIG. 9 and Table 2). $K_a$ values determined by linear regression analysis are displayed in Table 2. Mannan, a known ligand for DC-SIGN, was able to compete with 2,6-sialylated Fc for its binding to the transfected CHO cells, demonstrating that the binding sites for these two ligands on the CRD are likely to be overlapping. No binding was observed for fibrinogen, an abundant serum glycoprotein with a sialylated biantennary glycan composition similar to that found on the IgG Fc, but lacking the highly ordered structure seen for the Fc linked glycan (FIG. 9), indicating that the interactions between 2,6-sialylated Fc and these lectins required both the glycan and amino acid backbone for their specificity.

TABLE 2

$K_a$s of SIGN-R1, hDC-SIGN, and hFc•RIIb for sialylated asialylated IgG Fcs

| Receptor | 2, 6Fc | Asialylated FC |
|---|---|---|
| SIGN-R1 | $2.7 \times 10^{-6}$ | n.b. |
| hDC-SIGN | $3.6 \times 10^{-6}$ | n.b. |
| hFc•RIIb | $1.5 \times 10^{-5}$ | $1.6 \times 10^{-6}$ |

All patent and non-patent publications cited in this disclosure are incorporated herein in to the extent as if each of those patent and non-patent publications was incorporated herein by reference in its entirety. Further, even though the invention herein has been described with reference to particular examples and embodiments, it is to be understood that these examples and embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A method of identifying a compound useful to activate or suppress anti-inflammatory activity associated with IgG autoantibody-mediated inflammation, which comprises:

(a) contacting a test compound with a DC-SIGN receptor protein;

(b) measuring binding affinity of the test compound to the DC-SIGN receptor protein; and (c) selecting the test compound as a compound useful to activate or suppress anti-inflammatory activity associated with IgG autoantibody-mediated inflammation based on a measurable binding affinity of the test compound to the DC-SIGN receptor protein as compared to a control experiment in the absence of the test compound;

thereby identifying the compound.

2. The method of claim 1 wherein the DC-SIGN receptor protein is selected from the group consisting of SIGN-R, DC-SIGN and DC-SIGNR.

3. The method of claim 1 wherein step a) is carried out in the presence of $Ca^{++}$.

4. The method of claim 1 wherein the DC-SIGN receptor protein is provided as a DC-SIGN$^{(+)}$ cell.

5. The method of claim 4 wherein the DC-SIGN receptor protein is selected from the group consisting of SIGN-R, DC-SIGN and DC-SIGNR.

6. The method of claim 4 wherein the DC-SIGN$^{(+)}$ cell is provided as cultured cells transfected with a nucleic acid molecule recombinantly encoding a lectin domain selected from the group consisting of SIGN-R, DC-SIGN and DC-SIGNR.

7. The method of claim 1 wherein step a) is carried out in a cell-free environment.

8. The method of claim 7 wherein the DC-SIGN receptor type protein is selected from the group consisting of SIGN-R, DC-SIGN and DC-SIGNR.

9. The method of claim 4 wherein step a) is carried out in the presence of $Ca^{++}$.

10. The method of claim 1, wherein the test compound is an intravenous immunoglobin IVIG antibody preparation.

11. The method of claim 1, wherein the test compound is an Fc fragment.

12. The method of claim 1, wherein the test compound is an antibody comprising a carbohydrate chain comprising a galactose moiety attached to a terminal sialic acid moiety via α 2,6 sialylation.

13. The method of claim 1, wherein the test compound is an Fc fragment comprising a carbohydrate chain comprising a galactose moiety attached to a terminal sialic acid moiety via α 2,6 sialylation.

14. The method of any one of claims 1-9 and 10-13, wherein the test compound is selected as a compound useful to activate anti-inflammatory activity associated with IgG autoantibody-mediated inflammation based on a measurable increase in binding affinity of the test compound to the DC-SIGN receptor protein as compared to the control experiment in the absence of the test compound.

15. The method of any one of claims 1-9 and 10-13, wherein the test compound is selected as a compound useful to suppress anti-inflammatory activity associated with IgG autoantibody-mediated inflammation based a measurable decrease in binding affinity of the test compound to the DC-SIGN receptor protein as compared to the control experiment in the absence of the test compound.

* * * * *